US012569594B2

(12) United States Patent　　(10) Patent No.:　US 12,569,594 B2
Bahney et al.　　　　　　　　　(45) Date of Patent:　Mar. 10, 2026

(54) DECELLULARIZED TENDON MATRIX METHODS AND USES THEREOF

(71) Applicant: The Steadman Clinic and Steadman Philippon Research Institute, Vail, CO (US)

(72) Inventors: Chelsea S. Bahney, Edwards, CO (US); Peter J. Millett, Edwards, CO (US); David Bernholt, Avon, CO (US); Anna-Laura Nelson, Leadville, CO (US)

(73) Assignee: The Steadman Clinic and Steadman Philippon Research Institute, Vail, CO (US)

( * ) Notice: Subject to any disclaimer, the term of this patent is extended or adjusted under 35 U.S.C. 154(b) by 856 days.

(21) Appl. No.: 17/415,501

(22) PCT Filed: Dec. 20, 2019

(86) PCT No.: PCT/US2019/068112
§ 371 (c)(1),
(2) Date: Jun. 17, 2021

(87) PCT Pub. No.: WO2020/132608
PCT Pub. Date: Jun. 25, 2020

(65) Prior Publication Data
US 2022/0047775 A1　　Feb. 17, 2022

Related U.S. Application Data

(60) Provisional application No. 62/782,903, filed on Dec. 20, 2018, provisional application No. 62/890,865, filed on Aug. 23, 2019.

(51) Int. Cl.
*A61L 27/36*　　(2006.01)
*A61L 27/52*　　(2006.01)
*A61L 27/54*　　(2006.01)

(52) U.S. Cl.
CPC ....... *A61L 27/3662* (2013.01); *A61L 27/3687* (2013.01); *A61L 27/52* (2013.01); *A61L 27/54* (2013.01); *A61L 2300/404* (2013.01); *A61L 2300/414* (2013.01); *A61L 2430/40* (2013.01)

(58) Field of Classification Search
None
See application file for complete search history.

(56) References Cited

U.S. PATENT DOCUMENTS

| | | | | |
|---|---|---|---|---|
| 8,894,707 | B2 * | 11/2014 | Zhao | A61L 27/38 |
| | | | | 623/13.11 |
| 2006/0073592 | A1 | 4/2006 | Sun et al. | |
| 2013/0236439 | A1 | 9/2013 | Sun et al. | |
| 2014/0350677 | A1 | 11/2014 | Chang et al. | |
| 2016/0053250 | A1 | 2/2016 | Zylberberg et al. | |
| 2016/0166735 | A1 * | 6/2016 | Chang | A61L 27/54 |
| | | | | 424/530 |
| 2018/0133369 | A1 * | 5/2018 | Chang | A61L 27/386 |
| 2019/0070272 | A1 | 3/2019 | Sun et al. | |

FOREIGN PATENT DOCUMENTS

| | | |
|---|---|---|
| CN | 107 737 373 A | 2/2018 |
| JP | 2013-165740 A | 8/2013 |
| WO | 2017143344 A1 | 8/2017 |
| WO | 2020132608 A1 | 6/2020 |

OTHER PUBLICATIONS

International Search Report mailed May 22, 2020 for International Patent Application No. PCT/US2019/068112.
Written Opinion mailed May 22, 2020 for International Patent Application No. PCT/US2019/068112.
Ning et al., Preparation and characterization of decellularized tendon slices for tendon tissue engineering. J Biomed Mater Res Part A, Jun. 2012, vol. 100, No. 6, p. 1448-56 (Abstract only).
International Search Report mailed Oct. 20, 2021 for International Patent Application No. PCT/US2021/038165.
Written Opinion mailed Oct. 20, 2021 for International Patent Application No. PCT/US2021/038165.
Search Report issued in corresponding European Patent Application No. 19898521.0, dated Aug. 19, 2022, 10 pages.
Office Action issued in corresponding Canadian Application No. 3,124,665, dated Mar. 27, 2024, 4 pages.
English translation of Notice of Reasons for Rejection issued in corresponding Japanese Application No. 2021-536113, dated Oct. 31, 2023, 5 pages.
Examination Report issued in corresponding Australian Application No. 2019404558, dated Jul. 29, 2024, 3pages.
Office Action issued in corresponding European Application No. 19898521.0, dated Mar. 4, 2024, 8 pages.

* cited by examiner

*Primary Examiner* — Russell G Fiebig
(74) *Attorney, Agent, or Firm* — Morgan, Lewis & Bockius LLP

(57) ABSTRACT

Methods of making decellularized tendon matrix (DTM) and DTM hydrogels are provided. These compositions and hydrogels are useful for repairing tendon injuries and in some cases may be used by injection, arthroscopic procedures, or as adjuncts to traditional surgical repair.

22 Claims, 21 Drawing Sheets

CHRONIC SHOULDER INJURY

Supraspinatus

Tuberosity

PLACEMENT OF DTM

DTM

Tuberosity  Supraspinatus

RECONSTRUCTION

DECELLULARIZED TENDON MATRIX METHODS AND USES THEREOF

CROSS-REFERENCE TO RELATED APPLICATIONS

This application is the U.S. national stage patent application under 35 U.S.C. § 371 of international application No. PCT/US2019/068112, filed on Dec. 20, 2019, claiming the benefit of U.S. Provisional Application No. 62/782,903, filed on Dec. 20, 2018, and U.S. Provisional Application No. 62/890,865, filed on Aug. 23, 2019, each of which is incorporated herein by reference in its entirety.

FIELD OF THE INVENTION

The invention described herein relates generally to decellularized tendon matrix, and methods of making and using decellularized tendon matrix.

BACKGROUND OF THE INVENTION

Regenerative medicine is an emerging discipline that has identified many uses for extracellular matrix materials. Tendons are fibrous connective tissues that connect muscle to bone. The connection between muscle and tendon is referred to as the myotendinous junction or as the tendon-muscle insertion point; the connection between tendon and bone is referred to as the osteotendinous junction. This is also known as the tendon insertion or the enthesis, and disease here is known as enthesopathy. This latter connection, the junction between tendon and bone, where tendon collagen fibrils insert into the bone matrix, is a common location of tendon injury. Commonly these injuries arise from overuse, from intrinsic tendon degeneration (tendinopathy) or from traumatic injuries.

Tendon injury leads to well characterized cellular and tissue changes that together result in altered biomechanical properties of the tendon. E.g., Arya and Kulig, *J. Appl. Physiol.* 108:670-675 (2010). Injury from overuse, intrinsic degeneration or from trauma may be manifest as a tendon tear. Tears are categorized by severity, from first degree minimal tears, to second degree moderate to severe tears, and finally third degree complete tears. They are also classified in other ways, such as partial or complete, in different anatomical areas of the body, such as the rotator cuff, Achilles tendon, quadriceps tendon, biceps tendon, and others.

Tears generally require surgical intervention. In some aspects, the present invention provides methods to produce compositions useful for repairing tendon injuries, including tears.

Furthermore, compositions of the invention induce tissue regeneration accelerating tendon regrowth, tendon healing, or reconstitution of the native tendon insertion into bone. The methods of the invention preserve endogenous growth factors present in the extracellular matrix and provide compositions for tendon regeneration, healing, and/or repair.

SUMMARY OF THE INVENTION

In an aspect, the invention provides a method of producing a composition comprising matrix metalloproteinase (MMP) and/or collagenase digested tendon tissue, an antimicrobial agent, and a sterile aqueous carrier solution.

In another aspect, the invention provides decellularized tendon matrix (DTM) composition wherein the DTM composition is prepared by a process comprising the steps of: (i) mincing a tendon tissue specimen; (ii) decellularizing the minced tendon tissue specimen; (iii) milling; (iv) digesting; (v) stopping and neutralizing; (vi) washing; and, (vii) lyophilizing.

In an aspect, the invention provides methods for preparing decellularized tendon matrix that preserves growth factors.

In some embodiments, the disclosure provide a decellularized tendon matrix (DTM) composition comprising matrix metalloproteinase (MMP) digested tendon tissue. In some embodiments, the disclosure provide a decellularized tendon matrix (DTM) composition comprising collagenase digested tendon tissue. In some embodiments, the composition comprises a collagen digestate. In some embodiments, the composition further comprises an antimicrobial agent. In some embodiments, the composition further comprises a sterile aqueous carrier solution. In some embodiments, the decellularized tendon matrix (DTM) is protein rich retains at least 50% of the growth factors present in the minced tendon tissue. In some embodiments, the composition is moldable. In some embodiments, the composition is able to substantially adhering to an anatomical topography.

In some embodiments, the disclosure also provides a method of making a decellularized tendon matrix (DTM) composition, the method comprising one or more steps selected from mincing a tendon tissue specimen; decellularizing the minced tendon tissue specimen; milling; digesting; stopping and neutralizing; washing; and lyophilizing. In some embodiments, the method comprises digesting with a matrix metalloproteinase (MMP) selected from the group consisting of MMP-2, MMP-9, MMP-14, or combinations thereof. In some embodiments, the method comprises digesting with a collagenase described herein. In some embodiments, the method comprises decellularizing with a DNase described herein.

The disclosure also provides a decellularized tendon matrix (DTM) composition wherein the DTM composition is prepared by a process comprising one or more steps selected from: mincing a tendon tissue specimen; decellularizing the minced tendon tissue specimen; digesting; and lyophilizing. In some embodiments, the disclosure provides a decellularized tendon matrix (DTM) composition wherein the DTM composition is prepared by a process comprising one or more steps selected from: mincing a tendon tissue specimen; decellularizing the minced tendon tissue specimen; milling; digesting; stopping; neutralizing; washing; and lyophilizing. In some embodiments, the decellularizing step comprises exposing the minced tendon tissue specimen to a solution comprising one or more components selected from a chaotropic salt, a non-ionic detergent, a zwitterionic detergent, a cationic detergent, an anionic detergent, or combinations thereof. In some embodiments, the decellularizing step comprises exposing the minced tendon tissue specimen to a DNase, an RNase, or a combination thereof. In some embodiments, the decellularizing step comprises exposing the minced tendon tissue specimen to a DNase. In some embodiments, the digesting step comprises digesting with a solution comprising a matrix metalloproteinase (MMP). In some embodiments, the matrix metalloproteinase (MMP) is selected from MMP-2, MMP-9, MMP-14, or combinations thereof. In some embodiments, the stopping and/or neutralizing step comprises stopping and/or neutralizing with a solution comprising one or more protease inhibitors selected from TAPI-O, TAPI-1, TAPI-2, marimastat, phosphoramidon, luteolin, PMSF, pepstatin A, leupeptin, E-64, sodium orthovanadate, or combinations thereof.

The disclosure also provides a method of stimulating tendon regeneration, the method comprising one or more steps selected from: resuspending a DTM composition described herein in a pharmaceutically acceptable carrier; and applying the resuspended DTM composition to a tendon site in need of stimulating tendon regeneration. In some embodiments, the resuspended DTM composition is moldable. In some embodiments, the resuspended DTM composition has a putty consistency. In some embodiments, the resuspended DTM composition is a gel. In some embodiments, the resuspended DTM composition is a paste. In some embodiments, the resuspended DTM composition is thixotropic. In some embodiments, the resuspended DTM composition is viscoelastic. In some embodiments, the resuspended DTM composition is injectable. In some embodiments, the resuspended DTM composition is spreadable.

The disclosure also provides a decellularized tendon matrix (DTM) hydrogel, comprising a resuspended DTM composition described herein, and one or more of 1-ethyl-3-[3-dimethylam inopropyl]carbodiimide (EDC) and PEG-N-hydroxysuccinimide (NHS) ester. In some embodiments, the hydrogel is moldable. In some embodiments, the hydrogel has a putty consistency. In some embodiments, the hydrogel is a paste. In some embodiments, the hydrogel is thixotropic. In some embodiments, the hydrogel is viscoelastic. In some embodiments, the hydrogel is injectable. In some embodiments, the hydrogel is spreadable.

The disclosure also provides a soft-cast decellularized tendon matrix (DTM) object, wherein the soft-cast object is prepared by a process comprising one or more steps of: resuspending a decellularized tendon matrix (DTM) composition described herein in a physiological buffer; mixing the DTM composition with PEG-N-hydroxysuccinimide (NHS) ester to produce a soft hydrogel; transferring the soft hydrogel to a three dimensional mold; curing the polymerization reaction; and inactivating the polymerization reaction.

The disclosure also provides a decellularized tendon matrix (DTM) hydrogel comprising a resuspended DTM composition described herein, further comprising 1-ethyl-3-[3-dimethylam inopropyl]carbodiim ide (EDC) and a water-soluble coupling agent selected from N-hydroxysuccinimide (NHS) or a N-hydroxysulfosuccinimide (sulfoNHS) in conjunction with the (EDC) coupling agent.

The disclosure also provides a method of treating a tendon tear and/or stimulating tendon regeneration in a subject, the method comprising one or more of: obtaining a decellularized tendon matrix (DTM) composition comprising matrix metalloproteinase (MMP) or collagenase digested tendon tissue; resuspending the DTM composition in a pharmaceutically acceptable carrier; and applying the resuspended DTM composition to a tendon site in need of stimulating tendon regeneration.

the disclosure also provides a decellularized tendon matrix produced from a native tendon, the decellularized tendon matrix comprising greater than 90% by weight of TGF-β in the native tendon. In some embodiments, the decellularized tendon matrix comprises greater than 95% by weight of TGF-β in the native tendon. In some embodiments, the decellularized tendon matrix comprises greater than 99% by weight of TGF-β in the native tendon. In some embodiments, the decellularized tendon matrix of any one of claims 18-20, comprises less than 5% by weight of cellular material in the native tendon. In some embodiments, the decellularized tendon matrix described herein comprises less than 2% by weight of cellular material in the native tendon. In some embodiments, the decellularized tendon matrix described herein comprises less than 1% by weight of cellular material in the native tendon. In some embodiments, the decellularized tendon matrix described herein comprises less than 0.1% by weight of cellular material in the native tendon. In some embodiments, the decellularized tendon matrix described herein comprises is substantially free of TGF-β producing cells. In some embodiments, the decellularized tendon matrix described herein comprises less than 5% by weight of DNA in the native tendon. In some embodiments, the decellularized tendon matrix described herein comprises less than 2% by weight of DNA in the native tendon. In some embodiments, the decellularized tendon matrix described herein comprises less than 1% by weight of DNA in the native tendon. In some embodiments, the decellularized tendon matrix described herein comprises less than 0.1% by weight of DNA in the native tendon. In some embodiments, the decellularized tendon matrix described herein is substantially free of DNA.

The disclosure also provides a method of producing a decellularized tendon matrix (DTM) composition from a tendon, the method comprising one or more of: decellularizing the tendon thereby producing a decellularized tendon; contacting the decellularized tendon with an enzymatic solution comprising a matrix metalloproteinase (MMP) to produce a digested, decellularized tendon; lyophilizing the digested, decellularized tendon to produce a lyophilized tendon; and reconstituting the lyophilized tendon to produce a decellularized tendon matrix. In some embodiments, the method comprises contacting the tendon with a DNase solution. In some embodiments, the DNase solution comprises about 10 to about 100 Units of DNase per milliliter of solvent, about 25 to about 75 Units of DNase per milliliter of solvent, about 40 to about 60 Units of DNase per milliliter of solvent, about 40 to about 60 Units of DNase per milliliter of solvent, or about 50 Units of DNase per milliliter of solvent. In some embodiments, the decellularizing comprises contacting the tendon with between about 4 milliliters and about 50 milliliters of the DNase solution per 1 gram of tendon. In some embodiments, the decellularizing comprises contacting the tendon with between about 5 milliliters and about 10 milliliters of the DNase solution per 1 gram of tendon. In some embodiments, the decellularizing comprises contacting the tendon with between about 10 milliliters and about 50 milliliters of the DNase solution per 1 gram of tendon. In some embodiments, the contacting occurs for a period of about 1 hour, and optionally occurs on a shaker. In some embodiments, the decellularizing further comprises washing the tendon with phosphate buffered saline. In some embodiments, the decellularizing further comprises filtering the tendon. In some embodiments, the lyophilizing comprises freezing the digested, decellularized tendon at minus 80° C. for at least about 30 minutes. In some embodiments, the method further comprises filtering through a 70 microm-eter strainer using centrifugation at between about 1500 G to about 2500 G for between about 1 minute and about 15 minutes. In some embodiments, the MMP comprises collagenase. In some embodiments, the collagenase is selected from the group consisting of Collagenase Type I, Collagenase Type III, and a combination thereof. In some embodiments, the concentration of the Collagenase Type I in the enzymatic solution is about 2 milligrams per milliliter. In some embodiments, the concentration of the Collagenase Type III in the enzymatic solution is about 1 milligram per milliliter. In some embodiments, the decellularized tendon is contacted with between about 10 milliliters and about 50 milliliters of the enzymatic solution per 1 gram of tendon. In some embodiments, the decellularized tendon is contacted with between about 5 milliliters and about 10 milliliters of the enzymatic solution per 1 gram of tendon. In some embodiments, the decellularized tendon is contacted with the enzymatic solution for about 24 hours. In some embodiments, the decellularized tendon is contacted with the enzymatic solution for about 12 hours. In some embodiments, the decellularized tendon is contacted with the enzymatic solution for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17, about 18 hours, about 19 hours, about 20 hours, about 21 hours, about 22 hours, about 23 hours, or about 24 hours. In some embodiments, the decellularized tendon is contacted with the enzymatic solution at about 37° C. In some embodiments, the reconstituting comprises mixing between about 2 microliters and about 5 microliters of solvent with about 1 milligram of lyophilized tendon.

6

1 hours, and 2 hours, while standard SDS and EDTA protocol calls for a 24-hour decellularization. DNA concentration was determined using DNEasy kits (Qiagen, n=3). All values were normalized to no decellularization. Tukey's HSD multiple comparison post-hoc testing shows no significant difference between the different times of DNAse treatment or decellularization by DNAse versus SDS and EDTA.

FIGS. 9A-H illustrate that Achilles tendon matrix has more protein content than patella tendon. The Achilles and Patellar tendons were divided into ⅓ sections consisting of the proximal, midcenter/middle, and distal ends of the tendon. (A-D) Total protein of the native tendons was measured using a BCA protein quantification kit (Thermo Scientific). (E-H) TGF-β was measured using a TGF-β magnetic bead panel Milliplex kit (Millipore Sigma, #TGFBMAG-64K-03). ANOVA shows no statistically significant differences between the regions of the tendons and therefore the entirety of the tendon can used through processing. When comparing the two different tendons (D) total protein is not different (P=0.93), but (H) TGF-β is statistically higher in Achilles than Patellar tendon (P=0.0045).

Figure 10:
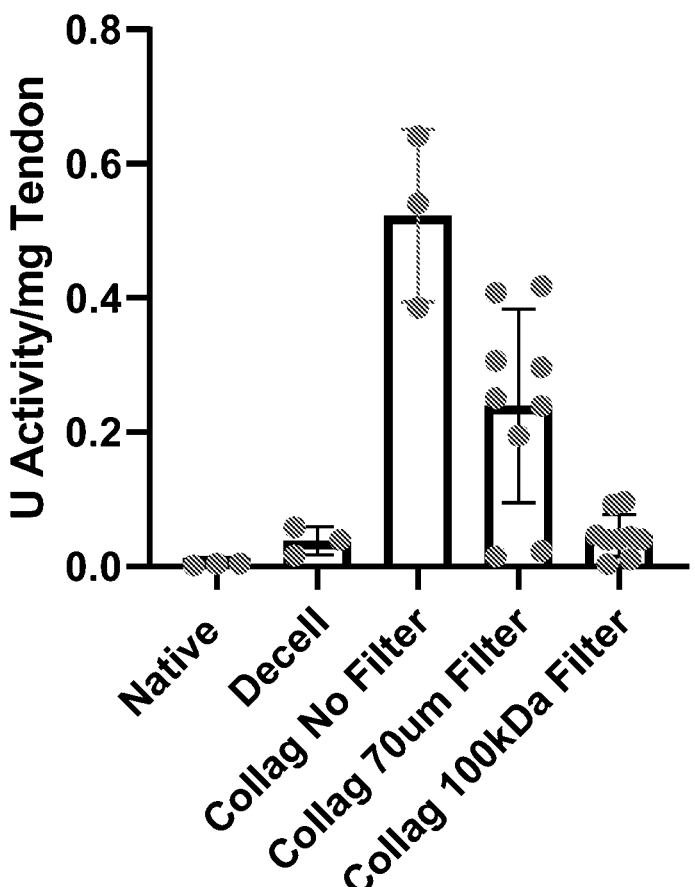

FIG. 10 illustrates that filtering effectively eliminates collagenase activity. Decellularized tendon was treated with collagenase to improve form-factor of DTM. 100 kDa filters were highly effective in eliminating the collagenase activity in the final product. ANOVA indicates that the groups have significant differences (F (4, 22)=18.06, p<0.0001). Importantly, there are no significant differences in collagenase activity between native and 100 kDa filtered samples.

Figure 11:
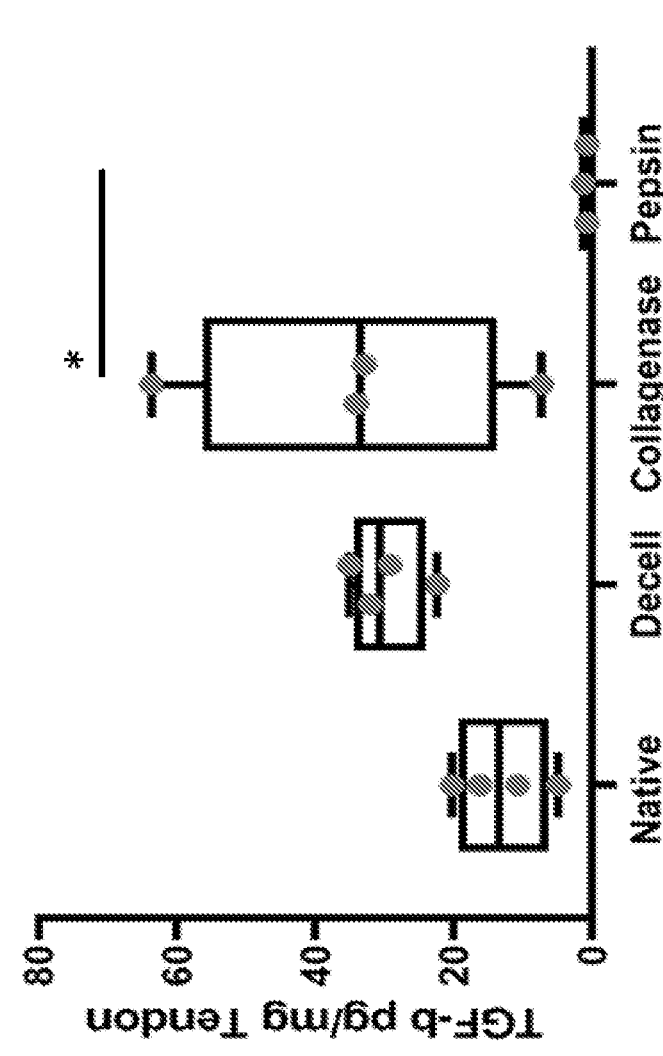

FIG. 11 illustrates that more bioactivity is retained in DTM than standard methods for decellularizing tendon with pepsin. Tendons were digested following decellularization, using a solution containing Collagenase Type 1 (92.5 g tendon/g Collagenase 1) and 3 (185 g tendon/1 g Col 3), or using Pepsin given previous published methodologies (Farnebo et. al 2014, PMID: 24341855). ANOVA indicated significant differences between groups, F (3,11)=5.056, p=0.0193. Tukey's HSD post hoc shows pepsin has significantly less TGF-β (P=0.0249).

Figure 12:
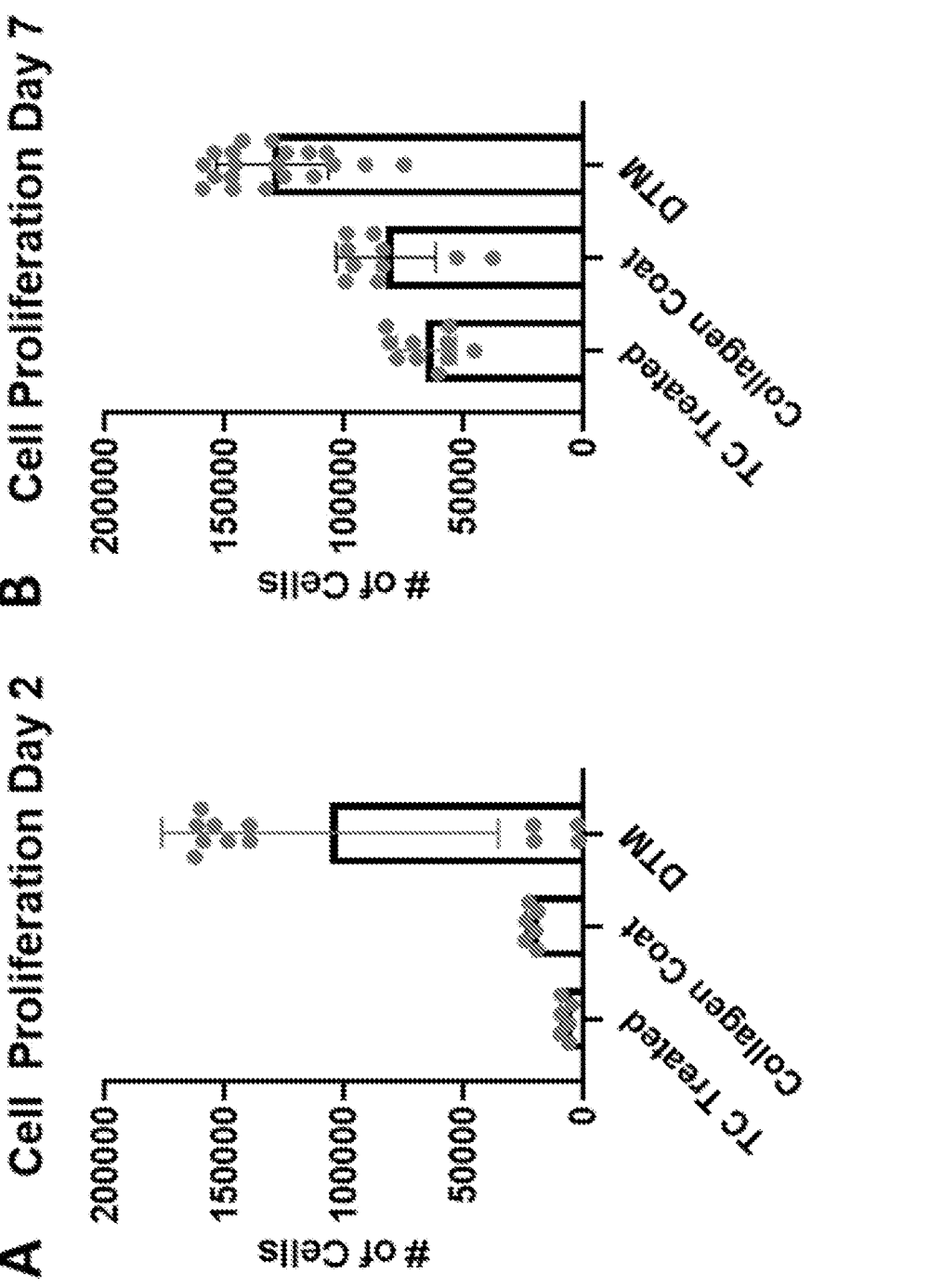
Figure 12:
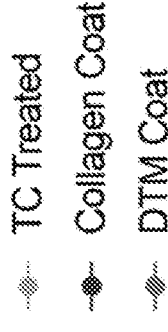
Figure 12:
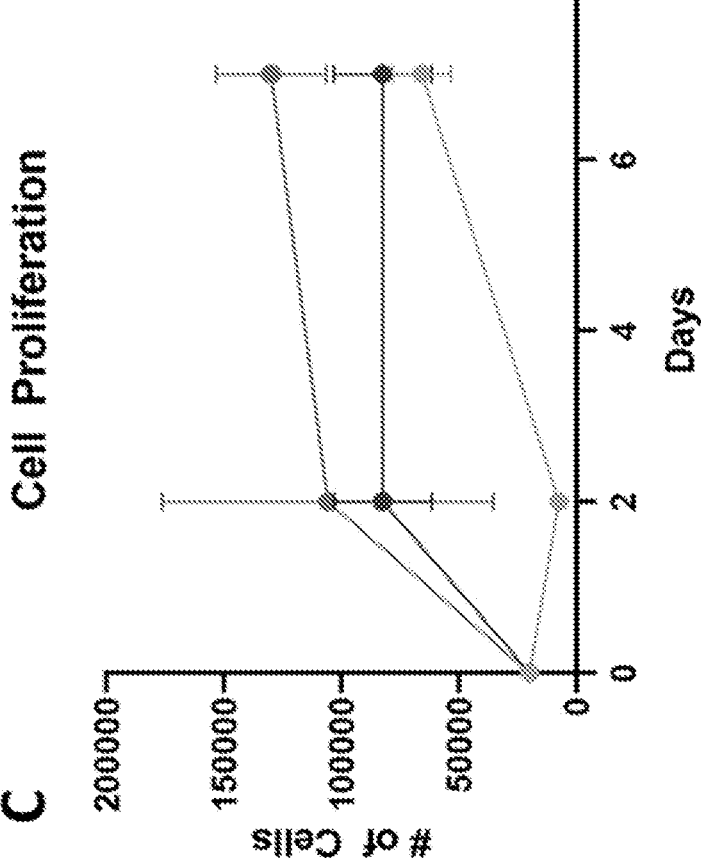
Figure 13:
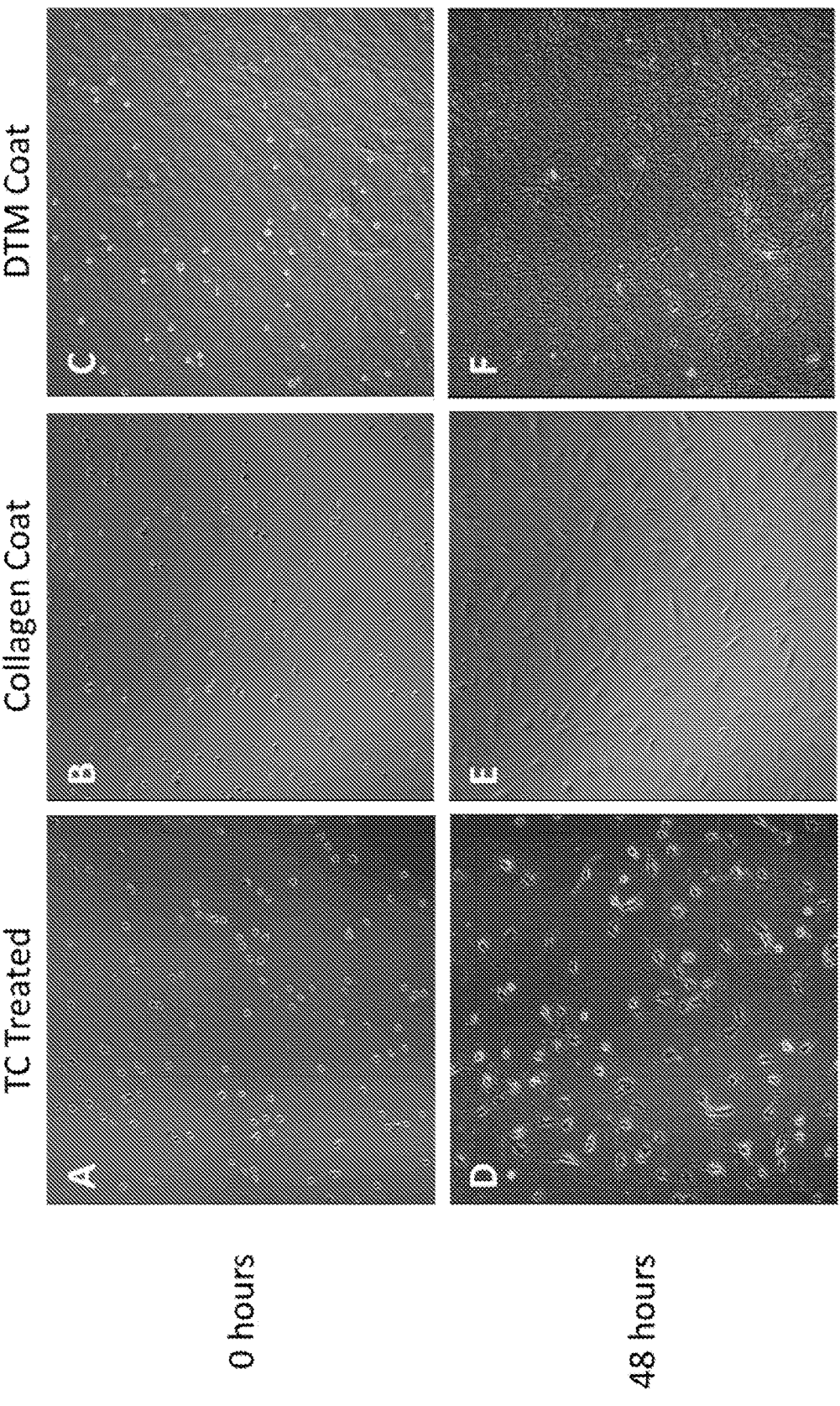

FIGS. 12A-C illustrate differences in proliferation of cells plated on different surfaces. Tissue culture plates were left untreated (control, "TC treated"), coated with collagen or with the DTM. Primary tenocytes (ZenBio #TEN-F) were plated at 20,000 cells/well and cell viability quantified using the Presto Blue (Thermo Fisher) at (A) 48 hours or (B) 7 days after plating, generating significantly different growth rates (C). (ANOVA=F (3,26)=10.6, p<0.0001).

FIGS. 13A-F illustrate differences in morphology and/or proliferation of cells plated on different surfaces. Tissue culture plates were left untreated (control, "TC treated"), coated with collagen or with the DTM. Primary tenocytes (ZenBio #TEN-F) were plated at 20,000 cells/well. Live cell images were taken by time laps video over 3 days showing significantly different cell morphology and proliferation rates (FIG. 6) between the different surface treatments. Still images from the live cell imaging were taken at 48 hours and show that tenocytes more rapidly adhere, proliferate and with increased focal adhesion and a more native like cell morphology on the DTM compared (F) to the standard tissue culture (D) or collagen coated plate (E).

Figure 14A:
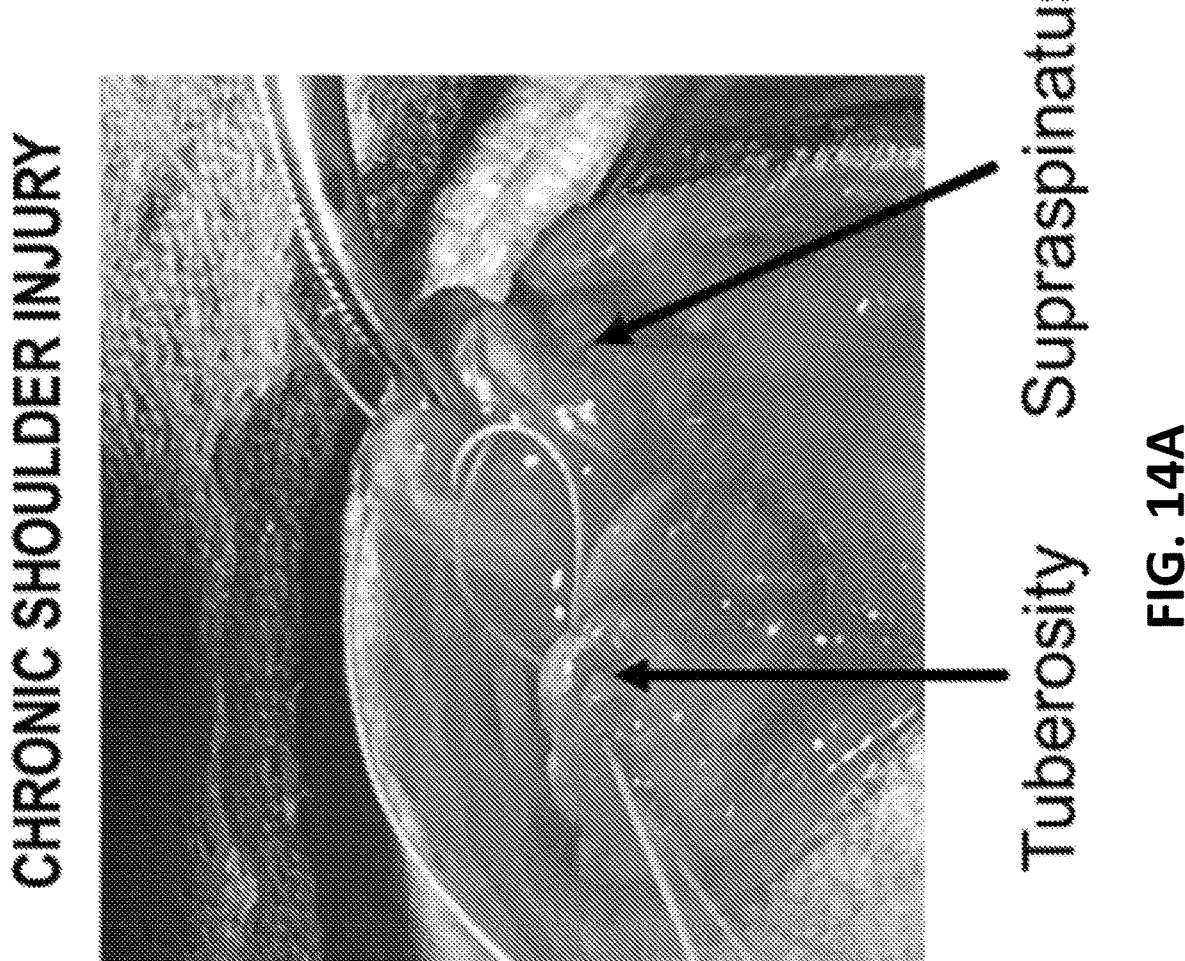
Figure 14B:
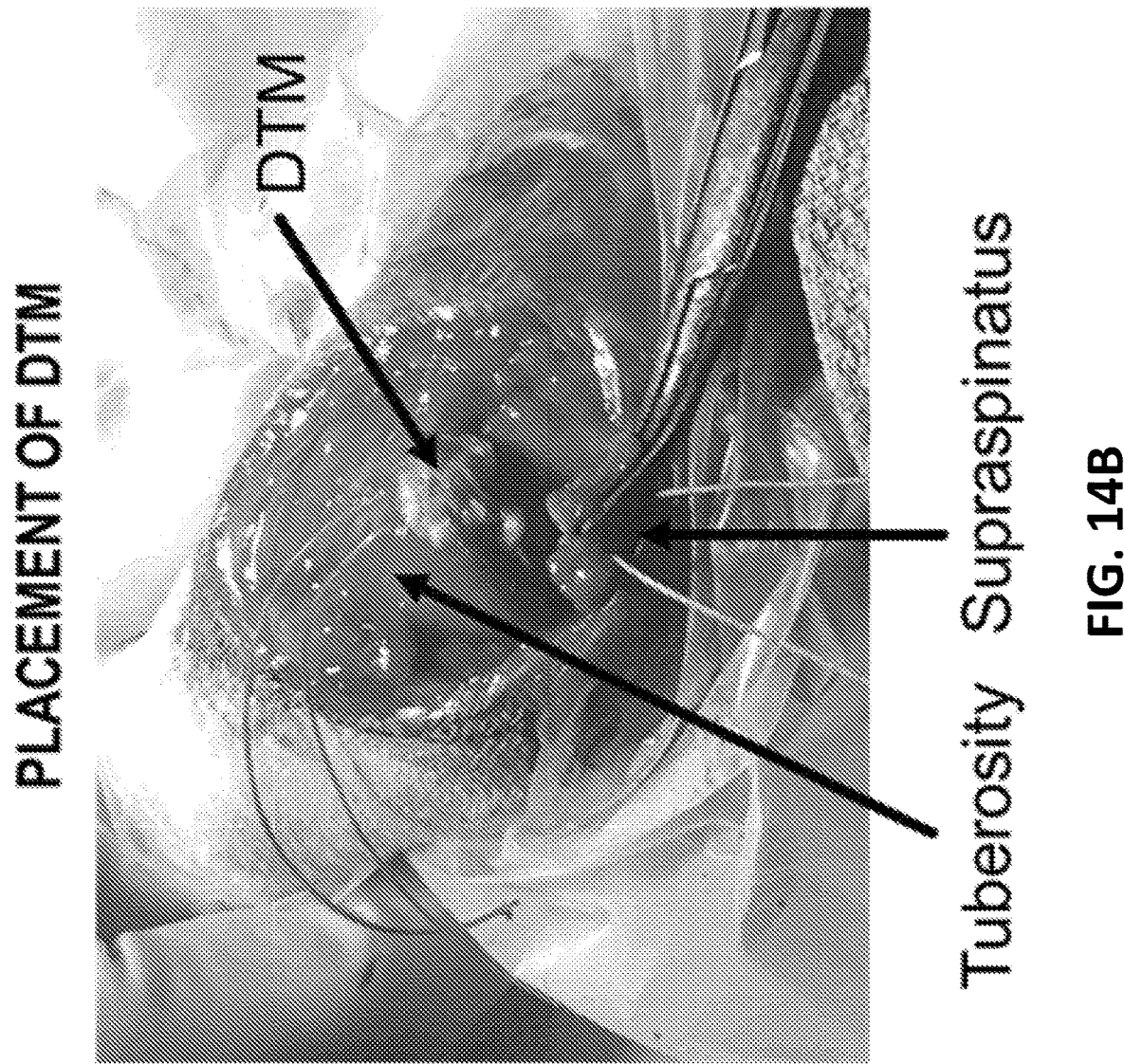
Figure 14C:
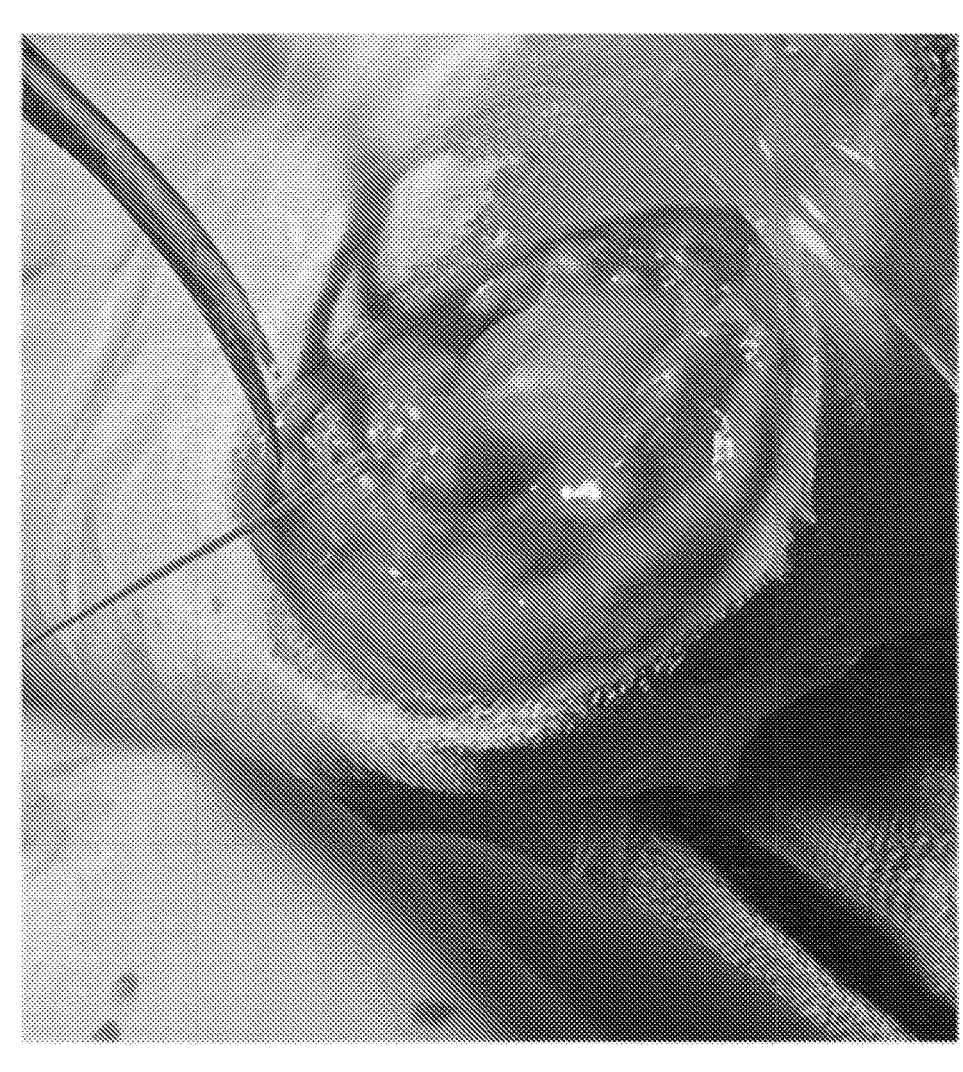

FIGS. 14A-C illustrates images of surgical application of DTM. DTM can be formed into a putty or an injectable solution. In this case the putty was placed upon the greater tuberosity and the supraspinatus surgically attached to secure the DTM.

Figure 15:
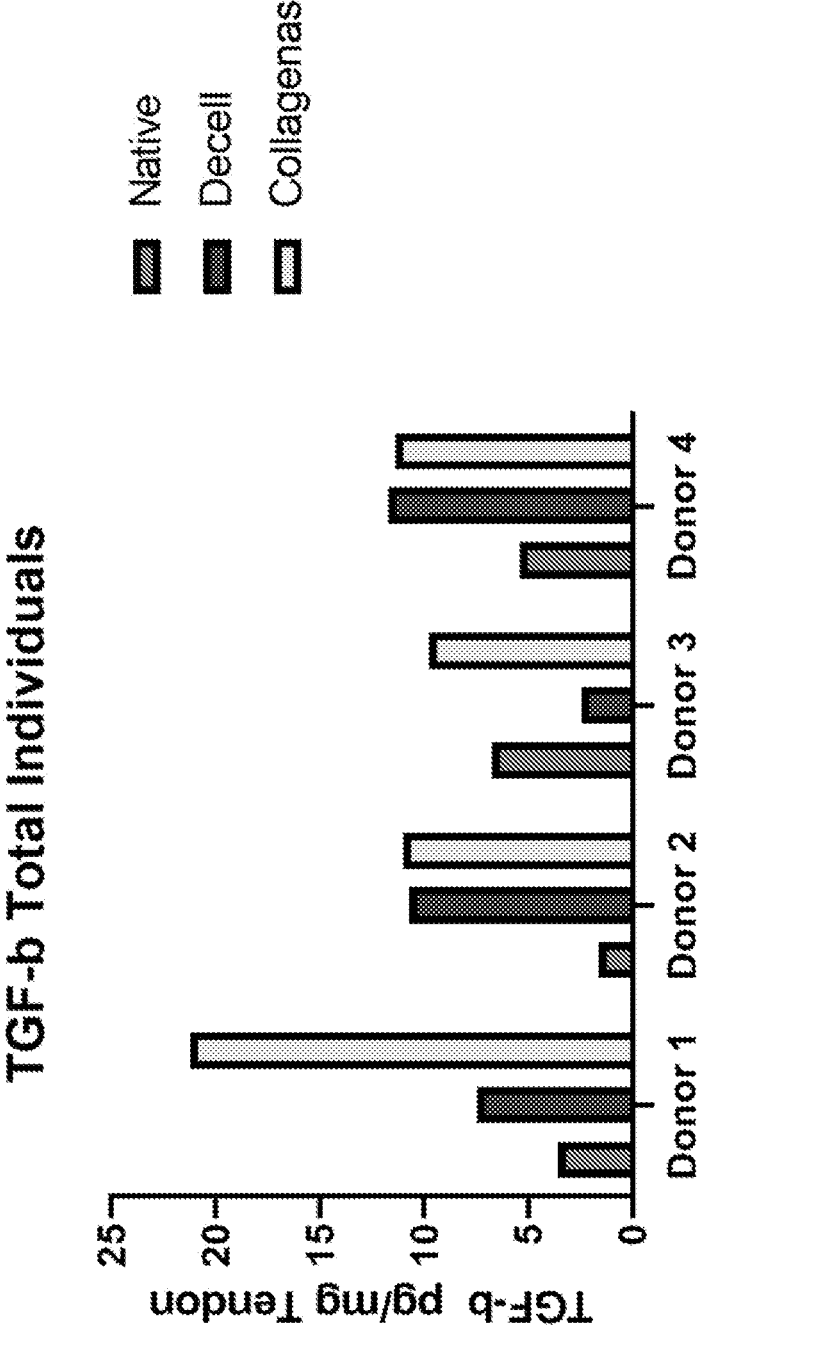

FIG. 15 illustrates the normalized TGFb content across four samples from four different donors, over the two processing steps. For each respective donor, the first column represents the amount of TGFb in the native tendon, the second column represents the amount of TGFb in the decellularized tendon, and the third column represents the amount of TGFb in the digested tendon.

DETAILED DESCRIPTION OF THE INVENTION

Unless defined otherwise, all technical and scientific terms used herein have the same meaning as is commonly understood by one of skill in the art to which this invention belongs. All patents and publications referred to herein are incorporated by reference in their entireties.

Definitions

The terms "co-administration," "co-administering," "administered in combination with," "administering in combination with," "simultaneous," and "concurrent," as used herein, encompass administration of two or more active pharmaceutical ingredients. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

"Treatment", "treating", "palliating" and "ameliorating", as used herein, are used interchangeably. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, "Donor" refers to a mammalian source for tendon connective tissue. The donor may be human or other animal source, including cadaveric tendon tissue. "Allogenic" donor tissue is donor tissue from a non-genetically identical member of the same species, for example, harvested from one human subject, then administering the resulting composition to a different human subject. Tendon connective tissue can be harvested from a donor that is of another species for use in the methods herein to produce decellularized tendon matrix compositions; such compositions are "xenographic" decellularized tendon matrix compositions. Preferred xenograph sources are pig, horse, cow, sheep, dog, and rodent. No matter the source, xenograph tendon tissue may be fresh or fresh-frozen tissue from a cadaveric donor. Preferred allograft sources are Achilles and patellar tendons. These tendons are readily available and are relatively large in size. They are also used widely in autograft and allograft application for the reconstruction of torn or damaged ligaments and tendons.

"Decellularization" as used herein refers to the general (at least 80%), nearly complete (at least 95%), or essentially complete (at least 99%) removal of cellular components of tendon connective tissue.

As used herein, "matrix metalloproteinases" refers to proteins of the matrix metalloproteinase (MMP) family. Matrix metalloproteinases (MMPs) comprise a large family of zinc-dependent endoproteinases, collectively capable of degrading all extracellular matrix (ECM) components. The term encompasses both the apo- and activated forms of each MMP family member. The term encompasses MMP-2, MMP-9, MMP-14, homologs, derivatives, and fragments thereof. Fanjul-Fernandez et al. summarize the mammalian MMP family in a review article, Biochim. Biophy. Acta 1803:3-19 (2010).

Various growth factors are known to the art, including: IGF-1 (Insulin-like growth factor 1, or somatomedin C), TGF-β (transforming growth factor beta), PDGF (Platelet-derived growth factor), VEGF (Vascular endothelial growth factor (VEGF), also known as vascular permeability factor (VPF)), bFGF (basic fibroblast growth factor, or fibroblast growth factor 2 (FGF2)), GDF-5 (Growth differentiation factor 5), GDF-6 (Growth differentiation factor 6), GDF-7 (Growth differentiation factor 7), HGF (hepatocyte growth factor or scatter factor). Without being bound by theory, the above non-limiting list of growth factors are known to the art to be found in the extracellular matrix of tendons.

The phrase "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio.

"Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the DTM ingredient, its use in the therapeutic compositions of the invention is contemplated. Additional active pharmaceutical ingredients, such as other drugs, can also be incorporated into the described compositions and methods.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, preferably from 0% to 10%, more preferably from 0% to 5% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

The terms "sequence identity," "percent identity," and "sequence percent identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. Suitable programs to determine percent sequence identity include for example the BLAST suite of programs available from the U.S. Government's National Center for Biotechnology Information BLAST web site. Comparisons between two sequences can be carried using either the BLASTN or BLASTP algorithm. BLASTN is used to compare nucleic acid sequences, while BLASTP is used to compare amino acid sequences. ALIGN, ALIGN-2 (Genentech, South San Francisco, California) or MegAlign, available from DNASTAR, are additional publicly available software programs that can be used to align sequences. One skilled in the art can determine appropriate parameters for maximal alignment by particular alignment software. In certain embodiments, the default parameters of the alignment software are used.

For the avoidance of doubt, it is intended that particular features (for example integers, characteristics, values, uses, diseases, formulae, compounds or groups) described in conjunction with a particular aspect, embodiment or example of the invention are to be understood as applicable to any other aspect, embodiment or example described herein unless incompatible therewith. Thus such features may be used where appropriate in conjunction with any of the definition, claims or embodiments defined herein. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any disclosed embodiments. The invention extends to any novel one, or novel combination, of the features disclosed in this specification (including any accompanying claims, abstract and drawings), or to any novel one, or any novel combination, of the steps of any method or process so disclosed.

Methods of Making Decellularized Tendon Matrix

One goal of the embodiments of the present disclosure is to produce a DTM that preserves growth factors, specifically TGF-β, in the matrix by developing a gentle and specific decellularization and digestion protocol. Traditionally detergents are harsh and can remove or denature proteins as well as the cellular material.

Typical digestion techniques for decellularized matrices use general proteinases, most commonly pepsin, which indiscriminately cleaves all proteins into small polypeptides. In this application enzymes specific for cleavage of collagen are used in order to break down the tendon into smaller parts that can subsequently form self-assembling peptide. Collagens, predominantly collagen type I, forms the structural backbone of tendon. By specifically cleaving the collagen we digest the tendon, but preserve the bioactivity of growth factors attached.

Collagenases are endopeptidases that digest the triple-helical native collagen fibrils commonly found in tendon. Collagenase cleaves the bond between a neutral amino acid (X) and glycine in the sequence Pro-X-Gly-Pro, which is found with high frequency in collagen. Bacterial collagenase, such as that made by *Clostridium histolyticum*, can attack almost all collagen types and degrades both water-insoluble native collagens and water-soluble denatured ones. Clostridial collagenases' ability to digest native, triple-helical types I, II, and III collagens through multiple scissions in the triple helix is a primary distinguishing factor. *Clostridium* collagenases represent unusually large metalloproteases, a family of proteases that shares a zinc-containing motif at the center of the active site (Gonzales and Robert-Baudouy 1996).

Matrix metalloproteinases (MMP) also have the ability to cleave collagen fibers in very specific sequences. Interstitial collagen types I, II and III are highly resistant to proteolytic attack, due to their triple helical structure, but can be cleaved by MMP collagenases at a specific sites. MMP-2 and -9 are closely related at the structural level and have demonstrated collagenase activity on collagen types I and III, generating the classic ¾ and ¼ fragments. MMP-1, MMP-8, MMP-13, the MT-MMPs also have some limited collagenase activity.

In an aspect, the invention provides a method of producing a composition comprising matrix metalloproteinase (MMP) digested tendon tissue, an antimicrobial agent, and a sterile aqueous carrier solution. In some embodiments, the matrix metalloproteinase (MMP) is selected from the group consisting of MMP-2, MMP-9, MMP-14, or combinations thereof. In an aspect, the MMP is engineered to be constitutively active. A person having skill in the art will appreciate that other MMPs can be used. Collagenases, the gelatinases, the stromelysins, and the membrane-type MMPs (MT-MMPs) can be used. In certain embodiments, collagenase can be used to decellularized a tendon and/or digest a decellularized tendon. As described herein, collagenases are capable of degrading triple-helical fibrillar collagens into distinctive ¾ and ¼ fragments. These collagens are the major components of bone, cartilage and dentin. Collagenases include Collagenase Type 1, Collagenase Type 2, Collagenase Type 3, Collagenase Type 8, Collagenase Type 13, Collagenase Type 14, and Collagenase Type 18.

Non-limiting examples of one or more MMPs that can be used include MMP1 (Interstitial collagenase, CLG, CLGN), MMP2 (Gelatinase-A, 72 kDa gelatinase), MMP3 (Stromelysin 1, CHDS6, MMP-3, SL-1, STMY, STMY1, STR1), MMP1 (Matrilysin, PUMP 1, MMP-7, MPSL1, PUMP-1), MMP8 (Neutrophil collagenase, CLG1, HNC, MMP-8, PMNL-CL), MMP9 (Gelatinase-B, 92 kDa gelatinase, CLG4B, GELB, MANDP2, MMP-9), MMP10 (Stromelysin 2, SL-2, STMY2), MMP11 (Stromelysin 3, SL-3, ST3, STMY3), MMP12 (Macrophage metalloelastase, HME, ME, MME, MMP-12), MMP13 (Collagenase 3, CLG3, MANDP1, MMP-13), MMP14 (MT1-MMP, MMP-14, MMP-X1, MT-MMP, MT-MMP 1, MT1-MMP, MT1MMP, MTMMP1, WNCHRS), MMP15 (MT2-MMP, MT2-MMP, MTMMP2, SMCP-2, MMP-15, MT2MMP), MMP16 (MT3-MMP, C8orf57, MMP-X2, MT-MMP2, MT-MMP3, MT3-MMP), MMP17 (MT4-MMP, MT4-MMP, MMP-17, MT4MMP, MTMMP4), MMP18 (Collagenase 4, xco14, xenopus collagenase), MMP19 (RASI-1, occasionally referred to as stromelysin-4, MMP18, RASI-1, CODA), MMP20 (Enamelysin, AI2A2, MMP-20), MMP21 (X-MMP, MMP-21, HTX7), MMP23A (CA-MMP), MMP23B (MIFR, MIFR-1, MMP22), MMP24 (MT5-MMP, MMP-24, MMP25, MT-MMP 5, MT-MMP5, MT5-MMP, MT5MMP, MTMMP5), MMP25 (MT6-MMP, MMP-25, MMP20, MMP20A, MMPL1, MT-MMP 6, MT-MMP6, MT6-MMP, MT6MMP, MTMMP6), MMP26 (Matrilysin-2, endometase), MMP27 (MMP-22, C-MMP, MMP-27), and MMP28 (Epilysin, EPILYSIN, MM28, MMP-25, MMP-28).

The concentration of collagenase used to enzymatically digest decellularized tendon can vary depending on the specific collagenase used. In certain embodiments Collagenase Type 1 can be used to enzymatically digest decellularized tendon. In certain embodiments Collagenase Type 3 can be used to enzymatically digest decellularized tendon. The concentration of collagenase used to enzymatically digest decellularized tendon can be about 0.1 milligram (mg)/milliliter (mL), about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1.0 mg/mL, about 1.1 mg/mL, about 1.2 mg/mL, about 1.3 mg/mL, about 1.4 mg/mL, about 1.5 mg/mL, about 1.6 mg/mL, about 1.7 mg/mL, about 1.8 mg/mL, about 1.9 mg/mL, about 2.0 mg/mL, about 2.1 mg/mL, about 2.2 mg/mL, about 2.3 mg/mL, about 2.4 mg/mL, about 2.5 mg/mL, about 2.6 mg/mL, about 2.7 mg/mL, about 2.8 mg/mL, about 2.9 mg/mL, about 3.0 mg/mL, about 3.1 mg/mL, about 3.2 mg/mL, about 3.3 mg/mL, about 3.4 mg/mL, about 3.5 mg/mL, about 3.6 mg/mL, about 3.7 mg/mL, about 3.8 mg/mL, about 3.9 mg/mL, about 4.0 mg/mL, about 5.0 mg/mL, about 6.0 mg/mL, about 7.0 mg/mL, about 8.0 mg/mL, about 9.0 mg/mL, or about 10.0 mg/mL. In certain embodiments, the concentration of collagenase used to enzymatically digest decellularized tendon is about 1.0 mg/mL. In other embodiments, the concentration of collagenase used to enzymatically digest decellularized tendon is about 2.0 mg/mL.

The antimicrobial agent is a suitable agent for use in a parenteral formulation, for example, an alkyl alcohol or an aryl alcohol, such as benzyl alcohol, chlorbutanol, or 2-ethoxyethanol. Amino aryl acid esters are also suitable, for example, methyl, ethyl, propyl, or butyl parabens and combinations thereof. Alkyl acids and aryl acids may also be suitable, for example, benzoic acid or sorbic acid; biguanides, for example, chlorhexidine or phenols, for example phenol or 3-cresol. In some embodiments, combinations of chemically compatible antimicrobial agents are used.

In an aspect, the present invention provides a decellularized tendon matrix (DTM) composition wherein the DTM composition is prepared by a process comprising the steps of: (i) mincing a tendon tissue specimen; (ii) decellularizing the minced tendon tissue specimen; (iii) digesting; and, (iv) lyophilizing.

In another aspect, the invention provides decellularized tendon matrix (DTM) composition wherein the DTM composition is prepared by a process comprising the steps of: (i) mincing a tendon tissue specimen; (ii) decellularizing the minced tendon tissue specimen; (iii) milling; (iv) digesting; (v) stopping and neutralizing; (vi) washing; and, (vii) lyophilizing.

In some cases, prior to decellularization, milling, digesting, lyophilizing, and/or washing the tendon matrix can be present in a portion of about 40%, about 45%, about 50%, about 55%, about 60%, about 65%, about 70%, about 75%, about 80%, about 85%, about 90%, about 95%, or about 99% by weight of the isolated tendon tissue.

In some cases, prior to decellularization, milling, digesting, lyophilizing, and/or washing, the tendon matrix can be present in a portion from about 50% to about 90%, about 50% to about 80%, about 50% to about 70%, about 50% to about 60%, about 50% to about 55%, 60% to about 90%, about 60% to about 80%, about 60% to about 70%, about 60% to about 65%, 70% to about 90%, about 70% to about 80%, about 70% to about 75%, 80% to about 90%, about 80% to about 85%, or about 85% to about 90% by weight of the isolated tendon tissue.

In some cases, prior to decellularization, milling, digesting, lyophilizing, and/or washing, the tendon matrix can be present in a portion of less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, or less than about 10% by weight of the isolated tendon tissue.

In some cases, prior to decellularization, milling, digesting, lyophilizing, and/or washing, the tendon matrix can be present in a portion of about 40%, about 45%, about 50%, about 55%, about 60%, about 65%, about 70%, about 75%, about 80%, about 85%, about 90%, about 95%, or about 99% by volume of the isolated tendon tissue.

In some cases, prior to decellularization, milling, digesting, lyophilizing, and/or washing, the tendon matrix can be present in a portion from about 50% to about 90%, about 50% to about 80%, about 50% to about 70%, about 50% to about 60%, about 50% to about 55%, 60% to about 90%, about 60% to about 80%, about 60% to about 70%, about 60% to about 65%, 70% to about 90%, about 70% to about 80%, about 70% to about 75%, 80% to about 90%, about 80% to about 85%, or about 85% to about 90% by volume of the isolated tendon tissue.

In some cases, prior to decellularization, milling, digesting, lyophilizing, and/or washing, the tendon matrix can be present in a portion of less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, or less than about 10% by volume of the isolated tendon tissue.

In some cases, after decellularization, milling, digesting, lyophilizing, and/or washing, the tendon matrix can be present in a portion of about 40%, about 45%, about 50%, about 55%, about 60%, about 65%, about 70%, about 75%, about 80%, about 85%, about 90%, about 95%, or about 99% by weight of the decellularized, milled, digested, lyophilized, and/or washed tendon tissue.

In some cases, after decellularization, milling, digesting, lyophilizing, and/or washing, the tendon matrix can be present in a portion from about 50% to about 90%, about 50% to about 80%, about 50% to about 70%, about 50% to about 60%, about 50% to about 55%, 60% to about 90%, about 60% to about 80%, about 60% to about 70%, about 60% to about 65%, 70% to about 90%, about 70% to about 80%, about 70% to about 75%, 80% to about 90%, about 80% to about 85%, or about 85% to about 90% by weight of the decellularized, milled, digested, lyophilized, and/or washed tendon tissue.

In some cases, after decellularization, milling, digesting, lyophilizing, and/or washing, the tendon matrix can be present in a portion of greater than about 99%, greater than about 95%, greater than about 90%, greater than about 85%, greater than about 80%, greater than about 75%, greater than about 70%, greater than about 65%, greater than about 60%, greater than about 55%, greater than about 50%, greater than about 45%, greater than about 40%, greater than about 35%, greater than about 30%, greater than about 25%, greater than about 20%, greater than about 15%, or greater than about 10% by weight of the decellularized, milled, digested, lyophilized, and/or washed tendon tissue.

In some cases, after decellularization, milling, digesting, lyophilizing, and/or washing, the tendon matrix can be present in a portion of about 40%, about 45%, about 50%, about 55%, about 60%, about 65%, about 70%, about 75%, about 80%, about 85%, about 90%, about 95%, or about 99% by volume of the decellularized, milled, digested, lyophilized, and/or washed tendon tissue.

In some cases, after decellularization, milling, digesting, lyophilizing, and/or washing, the tendon matrix can be present in a portion from about 50% to about 90%, about 50% to about 80%, about 50% to about 70%, about 50% to about 60%, about 50% to about 55%, 60% to about 90%, about 60% to about 80%, about 60% to about 70%, about 60% to about 65%, 70% to about 90%, about 70% to about 75%, 80% to about 90%, about 80% to about 85%, or about 85% to about 90% by volume of the decellularized, milled, digested, lyophilized, and/or washed tendon tissue.

In some cases, after decellularization, milling, digesting, lyophilizing, and/or washing, the tendon matrix can be present in a portion of greater than about 99%, greater than about 95%, greater than about 90%, greater than about 85%, greater than about 80%, greater than about 75%, greater than about 70%, greater than about 65%, greater than about 60%, greater than about 55%, greater than about 50%, greater than about 45%, greater than about 40%, greater than about 35%, greater than about 30%, greater than about 25%, greater than about 20%, greater than about 15%, or greater than about 10% by volume of the decellularized, milled, digested, lyophilized, and/or washed tendon tissue.

In an aspect, the decellularizing step comprises exposing the minced tendon tissue specimen to a solution comprising one or more component selected from the group consisting of a chaotropic salt, a non-ionic detergent, a zwitterionic detergent, a cationic detergent, an anionic detergent, or combinations thereof. In some aspects, the decellularizing step comprises one or more freeze/thaw cycles. In some aspects, the decellularizing step further comprises treatment with DNAase and/or RNAase. In some aspects, the decellularizing step further comprises one or more washes in a balance salt solution, for example, phosphate buffered saline of Hank's balanced salt solution.

In some embodiments, the minced tendon tissue specimen is rinsed in ultrapure water and then decellularized using a solution comprising 1% w/v sodium dodecyl sulfate (SDS) with using moderate stirring. In some embodiments, the moderate stirring is intermittent.

In another aspect, the minced tendon tissue specimen is decellularized using a solution comprising one or more of an ionic detergent, a nonionic detergent, an anionic detergent, or a cationic detergent. In some aspects, the decellularization solution further comprises a chaotropic salt. In some embodiments, the chaotropic salt is urea. In some embodiments, the decellularization solution comprises 0.5 M urea to 8 M urea. In some embodiments, the decellularization solution comprises 2 M to 5 M urea. In some embodiments the decellularization solution comprises about 3 M urea.

In some aspects, the decellularization solution comprises a surfactant, and a chaotropic salt. In some aspects, the decellularization solution further comprises an antifoam agent, for example, Antifoam 204.

In another aspect, the process further comprises a step to precipitate cellular proteins, the process further comprising treating the minced tendon tissue specimen with a concentrated cosmotropic solution. In some embodiments, the concentrated cosmotropic solution is ammonium sulfate. Cosmotropic salting out is accomplished, for example, according to the methods summarized by Wingfield, Curr. Protoc. Protein Sci., APPENDIX 3: Appendix-3F (2001).

Mincing may be accomplished using methods know to the art, for example, first removing sheath, adipose and synovial tissue from the tendon tissue specimen. Then, the tendon tissue specimen is minced into pieces roughly 1 to 4 mm$^3$ in size, then washed with phosphate-buffered saline (PBS).

In an aspect, the stopping and neutralizing step comprises stopping and neutralizing with a solution comprising one or more protease inhibitor selected from the group consisting of TAPI-0, TAPI-1, TAPI-2, marimastat, phosphoramidon, luteolin, PMSF, pepstatin A, leupeptin, E-64, sodium ortho-vanadate, or combinations thereof.

Decellularization may be monitored by methods known to the art, including, sectioning decellularized specimens and control specimens (i.e. untreated samples of starting donor tendon tissue), then staining with hematoxylin-eosin staining and Masson-Goldner's trichrome stain to detect the cellular components and collagen fibrous structures, respectively. DNA maybe extracted from decellularized samples and untreated, starting samples; decellularized samples should have at least 4-fold less DNA recovered for comparable starting weights. See, e.g., Seif-Naraghi et al., Acta Biomater. 8:3695-3703 (2012).

A decellularized tissue has the extracellular matrix (ECM) component of all or most regions of the tissue, including ECM components of the vascular tree. ECM components can include any one or any combination of the following: fibronectin, fibrillin, laminin, elastin, members of the collagen family (e.g., collagen I, III, and IV), ECM associated growth proteins including growth factors and cytokines, glycosaminoglycans, ground substance, reticular fibers and thrombospondin, which can remain organized as defined structures such as the basal lamina. Successful decellularization can be defined as the absence of detectable myofilaments, endothelial cells, smooth muscle cells, and nuclei in histologic sections using standard histological staining procedures or removal of over 97% of detectable DNA (e.g., as measured by fluorometric assay). Residual cell debris may be removed from the decellularized tissue.

The morphology and the architecture of the ECM can be maintained during and following the process of decellularization. "Morphology" as used herein refers to the overall shape of the of the ECM, while "architecture" as used herein refers to the exterior surface, the interior surface, and the ECM therebetween. The morphology and architecture of the ECM may be examined visually and/or histologically.

One or more compounds can be applied in or on a decellularized tissue to, for example, preserve the decellularized tissue, or to prepare the decellularized tissue for recellularization or integration or implant into a host. Such compounds include, but are not limited to, one or more growth factors (e.g., VEGF, DKK-1, FGF, BMP-1, BMP-4, SDF-1, IGF, and HGF), immune modulating agents (e.g., cytokines, glucocorticoids, IL2R antagonist, leucotriene antagonists), and/or factors that modify the coagulation cascade (e.g., aspirin, heparin-binding proteins, and heparin). In addition, a decellularized tissue may be further treated with, for example, irradiation (e.g., UV, gamma) to reduce or eliminate the presence of any type of microorganism remaining on or in a decellularized tissue.

In some aspects, the invention provides a method of making a decellularized tendon matrix (DTM) composition, the composition made using the method further comprises retaining at least 100, at least 99, at least 98, at least 97, at least 96, at least 95, at least 94, at least 93, at least 92, at least 91, at least 90% of the growth factors present in the minced tendon tissue. In some aspects, composition made using method of making a decellularized tendon matrix (DTM) composition, the composition made using the method further comprises retaining at least 85%, at least 80%, at least 75%, at least 70%, at least 65%, at least 60%, at least 55%, at least 50%, at least 45%, or at least 40% of the growth factors present in the minced tendon tissue. In some aspects, the invention provides a method of making a decellularized tendon matrix (DTM) composition, the composition made using the method further comprises retaining at least 99%, at least 98%, at least 97%, at least 96%, at least 95%, at least 94%, at least 93%, at least 92%, at least 91%, at least 90%, at least 89%, at least 88%, at least 87%, at least 86%, at least 85%, at least 84%, at least 83%, at least 82%, at least 81%, at least 80%, at least 79%, at least 78%, at least 77%, at least 45 76%, at least 75%, at least 74%, at least 73%, at least 72%, at least 71%, at least 70%, at least 69%, at least 68%, at least 67%, at least 66%, at least 65%, at least 64%, at least 63%, at least 62%, at least 61%, at least 60%, at least 59%, at least 58%, at least 57%, at least 56% at least 55%, at least 54%, at least 53%, at least 52%, at least 51%, at least 50%, at least 49%, at least 48%, at least 47%, at least 46%, at least 45%, at least 44%, at least 43%, at least 42%, at least 41%, at least 40%, at least 39%, at least 38%, at least 37%, at least 36%, at least 35%, at least 34%, at least 33%, at least 32%, at least 55 31%, at least 31%, at least 30%, at least 29%, at least 28%, at least 27%, at least 26% at least 25%, at least 24%, at least 23%, at least 22%, at least 21%, at least 20%, at least 19%, at least 18%, at least 17%, at least 16%, at least 15%, at least 14%, at least 13%, at least 12%, at least 11%, or at least 10% of the growth factors present in the minced tendon tissue. In some aspects, the invention provides a method of making a decellularized tendon matrix (DTM) composition, wherein the composition made using the method retained between about 70% and about 100% of the growth factors present in the minced tendon tissue before decellularizing. In some aspects, the invention provides a method of making a decellularized tendon matrix (DTM) composition, wherein the composition made using the method retained between about 70% and about 75% of the growth factors present in the minced tendon tissue before decellularizing. In some aspects, the invention provides a method of making a decellularized tendon matrix (DTM) composition, wherein the composition made using the method retained between about 75% and about 80% of the growth factors present in the minced tendon tissue before decellularizing. In some aspects, the invention provides a method of making a decellularized tendon matrix (DTM) composition, wherein the composition made using the method retained between about 80% and about 85% of the growth factors present in the minced tendon tissue before decellularizing. In some aspects, the invention provides a method of making a decellularized tendon matrix (DTM) composition, wherein the composition made using the method retained between about 85% and about 90% of the growth factors present in the minced tendon tissue before decellularizing. In some aspects, the invention provides a method of making a decellularized tendon matrix (DTM) composition, wherein the composition made using the method retained between about 90% and about 95% of the growth factors present in the minced tendon tissue before decellularizing. In some aspects, the invention provides a method of making a decellularized tendon matrix (DTM) composition, wherein the composition made using the method retained between about 95% and about 100% of the growth factors present in the minced tendon tissue before decellularizing. In some aspects, the invention provides a method of making a decellularized tendon matrix (DTM) composition, wherein the composition made using the method retained between about 75% and about 95% of the growth factors present in the minced tendon tissue before decellularizing. In some aspects, the invention provides a method of making a decellularized tendon matrix (DTM) composition, wherein the composition made using the method retained between about 70% and about 80% of the growth factors present in the minced tendon tissue before decellularizing. In some aspects, the invention provides a method of making a decellularized tendon matrix (DTM) composition, wherein the composition made using the method retained between about 80% and about 90% of the growth factors present in the minced tendon tissue before decellularizing. In some embodiments, the growth factors are selected from the group consisting of IGF-1, TGF-β, PDGF, VEGF, bFGF, GDF-5, GDF-6, GDF-7, HGF, and combinations thereof. In some embodiments, the growth factors include at least TGF-β.

In some aspects, the invention provides a method of making a decellularized tendon matrix (DTM) composition, the method further comprises retaining at least 90% of the cytokines present in the minced tendon tissue, wherein the growth factors are selected from the group consisting of IGF-1, TGF-β, PDGF, VEGF, bFGF, GDF-5, GDF-6, GDF-7, HGF, and combinations thereof. In some aspects, method of making a decellularized tendon matrix (DTM) composition, the method further comprises retaining at least 99%, at least 98%, at least 97%, at least 96%, at least 95%, at least 94%, at least 93%, at least 92%, at least 91%, at least 90%, at least 89%, at least 88%, at least 87%, at least 86%, at least 85%, at least 84%, at least 83%, at least 82%, at least 81%, at least 80%, at least 79%, at least 78%, at least 77%, at least 76%, at least 75%, at least 74%, at least 73%, at least 72%, at least 71%, at least 70%, at least 69%, at least 68%, at least 67%, at least 66%, at least 65%, at least 64%, at least 63%, at least 62%, at least 61%, at least 60%, at least 59%, at least 58%, at least 57%, at least 56% at least 55%, at least 54%, at least 53%, at least 52%, at least 51%, at least 50%, at least 49%, at least 48%, at least 47%, at least 46%, at least 45%, at least 44%, at least 43%, at least 42%, at least 41%, at least 40%, at least 39%, at least 38%, at least 37%, at least 36%, at least 35%, at least 34%, at least 33%, at least 32%, at least 31%, at least 31%, at least 30%, at least 29%, at least 28%, at least 27%, at least 26% at least 25%, at least 24%, at least 23%, at least 22%, at least 21%, at least 20%, at least 19%, at least 18%, at least 17%, at least 16%, at least 15%, at least 14%, at least 13%, at least 12%, at least 11%, or at least 10% of the growth factors present in the minced tendon tissue, wherein the growth factors are selected from the group consisting of IGF-1, TGF-β, PDGF, VEGF, bFGF, GDF-5, GDF-6, GDF-7, HGF, and combinations thereof.

In some aspects, the invention provides a method of making a decellularized tendon matrix (DTM) composition, the method further comprises retaining at least 90% of TGF-β present in the minced tendon tissue. In some aspects, the invention provides a method of making a decellularized tendon matrix (DTM) composition, the method further comprises retaining at least 95% of TGF-β present in the minced tendon tissue. In some aspects, the invention provides a method of making a decellularized tendon matrix (DTM) composition, the method further comprises retaining at least 99% of TGF-β present in the minced tendon tissue. In some aspects, method of making a decellularized tendon matrix (DTM) composition, the method further comprises retaining at least 99%, at least 98%, at least 97%, at least 96%, at least 95%, at least 94%, at least 93%, at least 92%, at least 91%, at least 90%, at least 89%, at least 88%, at least 87%, at least 86%, at least 85%, at least 84%, at least 83%, at least 82%, at least 81%, at least 80%, at least 79%, at least 78%, at least 77%, at least 76%, at least 75%, at least 74%, at least 73%, at least 72%, at least 71%, at least 70%, at least 69%, at least 68%, at least 67%, at least 66%, at least 65%, at least 64%, at least 63%, at least 62%, at least 61%, at least 60%, at least 59%, at least 58%, at least 57%, at least 56% at least 55%, at least 54%, at least 53%, at least 52%, at least 51%, at least 50%, at least 49%, at least 48%, at least 47%, at least 46%, at least 45%, at least 44%, at least 43%, at least 42%, at least 41%, at least 40%, at least 39%, at least 38%, at least 37%, at least 36%, at least 35%, at least 34%, at least 33%, at least 32%, at least 31%, at least 31%, at least 30%, at least 29%, at least 28%, at least 27%, at least 26% at least 25%, at least 24%, at least 23%, at least 22%, at least 21%, at least 20%, at least 19%, at least 18%, at least 17%, at least 16%, at least 15%, at least 14%, at least 13%, at least 12%, at least 11%, or at least 10% by weight of TGF-β in the native tendon.

In some aspects, method of making a decellularized tendon matrix (DTM) composition, the method further comprises retaining at least 85%, at least 80%, at least 75%, at least 70%, at least 65%, at least 60%, at least 55%, at least 50%, at least 45%, or at least 40% of the growth factors present in the minced tendon tissue, wherein the growth factors are selected from the group consisting of IGF-1, TGF-0, PDGF, VEGF, bFGF, GDF-5, GDF-6, GDF-7, HGF, and combinations thereof.

In some aspects, method of making a decellularized tendon matrix (DTM) composition, the method further comprises increasing the concentration of growth factors present in the decellularized tissue or DTM by at least 500%, at least 250%, at least 200%, at least 150%, at least 100%, at least 95%, at least 90%, at least 85%, at least 80%, at least 75%, at least 70%, at least 65%, at least 60%, at least 55%, at least 50%, at least 45%, at least 40%, at least 35%, at least 30%, at least 25%, at least 20%, at least 15%, at least 10%, at least 5%, wherein the growth factors are selected from the group consisting of IGF-1, TGF-β, PDGF, VEGF, bFGF, GDF-5, GDF-6, GDF-7, HGF, and combinations thereof.

In an aspect, the composition retains 2 or more of the above growth factors, 3 or more of the above growth factors, 4 or more of the above growth factors, 5 or more of the above growth factors, 6 or more of the above growth factors, 7 or more of the above growth factors. In an aspect, the composition retains HGF and one or more growth factors selected from the group consisting of IGF-1, TGF-0, PDGF, VEGF, bFGF, GDF-5, GDF-6, and GDF-7. In an aspect the composition retains IGF-1 and HGF.

In an aspect, the DTM composition further comprises retaining at least at least 85%, at least 84%, at least 83%, at least 82%, at least 81%, at least 80%, at least 79%, at least 78%, at least 77%, at least 76%, at least 75%, at least 74%, at least 73%, at least 72%, at least 71%, at least 70%, at least 69%, at least 68%, at least 67%, at least 66%, at least 65%, at least 64%, at least 63%, at least 62%, at least 61%, at least 60%, at least 59%, at least 58%, at least 57%, at least 56% at least 55%, at least 54%, at least 53%, at least 52%, at least 51%, at least 50%, at least 49%, at least 48%, at least 47%, at least 46%, at least 45%, at least 44%, at least 43%, at least 42%, at least 41%, at least 40%, at least 39%, at least 38%, at least 37%, at least 36%, at least 35%, at least 34%, at least 33%, at least 32%, at least 31%, at least 31%, at least 30%, at least 29%, at least 28%, at least 27%, at least 26% at least 25%, at least 24%, at least 23%, at least 22%, at least 21%, at least 20%, at least 19%, at least 18%, at least 17%, at least 16%, at least 15%, at least 14%, at least 13%, at least 12%, at least 11%, or at least 10% of the IGF-1 and HGF present in the minced tendon tissue.

In some aspects, the invention provides a method of making a decellularized tendon matrix (DTM) composition, the method further comprises removing at least 90% of cellular material present in the minced tendon tissue. In some aspects, the invention provides a method of making a decellularized tendon matrix (DTM) composition, the method further comprises removing at least 95% of cellular material present in the minced tendon tissue. In some aspects, the invention provides a method of making a decellularized tendon matrix (DTM) composition, the method further comprises removing at least 99% of cellular material present in the minced tendon tissue. In some aspects, method of making a decellularized tendon matrix (DTM) composition, the method further comprises removing at least 99%, at least 98%, at least 97%, at least 96%, at least 95%, at least 94%, at least 93%, at least 92%, at least 91%, at least 90%, at least 89%, at least 88%, at least 87%, at least 86%, at least 85%, at least 84%, at least 83%, at least 82%, at least 81%, at least 80%, at least 79%, at least 78%, at least 77%, at least 76%, at least 75%, at least 74%, at least 73%, at least 72%, at least 71%, at least 70%, at least 69%, at least 68%, at least 67%, at least 66%, at least 65%, at least 64%, at least 63%, at least 62%, at least 61%, at least 60%, at least 59%, at least 58%, at least 57%, at least 56% at least 55%, at least 54%, at least 53%, at least 52%, at least 51%, at least 50%, at least 49%, at least 48%, at least 47%, at least 46%, at least 45%, at least 44%, at least 43%, at least 42%, at least 41%, at least 40%, at least 39%, at least 38%, at least 37%, at least 36%, at least 35%, at least 34%, at least 33%, at least 32%, at least 31%, at least 31%, at least 30%, at least 29%, at least 28%, at least 27%, at least 26% at least 25%, at least 24%, at least 23%, at least 22%, at least 21%, at least 20%, at least 19%, at least 18%, at least 17%, at least 16%, at least 15%, at least 14%, at least 13%, at least 12%, 11%, or at least 10% by weight of cellular material in the native tendon. In certain embodiments, the invention provides a method of making a decellularized tendon matrix (DTM) composition, and the DTM is substantially free of cellular material. In certain embodiments, the invention provides a method of making a decellularized tendon matrix (DTM) composition, and the DTM is substantially free of TGF-β producing cells.

In some aspects, the invention provides a method of making a decellularized tendon matrix (DTM) composition, the method further comprises removing at least 90% of nucleic acids (e.g., DNA or RNA) present in the minced tendon tissue. In some aspects, the invention provides a method of making a decellularized tendon matrix (DTM) composition, the method further comprises removing at least 95% of nucleic acids (e.g., DNA or RNA) present in the minced tendon tissue. In some aspects, the invention provides a method of making a decellularized tendon matrix (DTM) composition, the method further comprises removing at least 99% of nucleic acids (e.g., DNA or RNA) present in the minced tendon tissue. In some aspects, method of making a decellularized tendon matrix (DTM) composition, the method further comprises removing at least 99%, at least 98%, at least 97%, at least 96%, at least 95%, at least 94%, at least 93%, at least 92%, at least 91%, at least 90%, at least 89%, at least 88%, at least 87%, at least 86%, at least 85%, at least 84%, at least 83%, at least 82%, at least 81%, at least 80%, at least 79%, at least 78%, at least 77%, at least 76%, at least 75%, at least 74%, at least 73%, at least 72%, at least 71%, at least 70%, at least 69%, at least 68%, at least 67%, at least 66%, at least 65%, at least 64%, at least 63%, at least 62%, at least 61%, at least 60%, at least 59%, at least 58%, at least 57%, at least 56% at least 55%, at least 54%, at least 53%, at least 52%, at least 51%, at least 50%, at least 49%, at least 48%, at least 47%, at least 46%, at least 45%, at least 44%, at least 43%, at least 42%, at least 41%, at least 40%, at least 39%, at least 38%, at least 37%, at least 36%, at least 35%, at least 34%, at least 33%, at least 32%, at least 31%, at least 31%, at least 30%, at least 29%, at least 28%, at least 27%, at least 26% at least 25%, at least 24%, at least 23%, at least 22%, at least 21%, at least 20%, at least 19%, at least 18%, at least 17%, at least 16%, at least 15%, at least 14%, at least 13%, at least 12%, at least 11%, or at least 10% by weight of nucleic acids (e.g., DNA or RNA) in the native tendon. In certain embodiments, the invention provides a method of making a decellularized tendon matrix (DTM) composition, and the DTM is substantially free of nucleic acids (e.g., DNA or RNA).

A variety of methods are known to the art, for example, those summarized by Gilpin and Yang, Biomed. Res. Int. 2017: 9831534 (2017). Many methods comprise aggressive detergent extractions and prolonged treatment with promiscuous proteases, for example, pepsin, at extreme, non-physiological pHs. The methods and processes of the present invention differ from those known to the art, by employing less promiscuous proteases that are active at physiological pHs. Without being bound by theory, the methods and processes of the present invention are less protein denaturing and preserve more functional growth factors in the decellularized tendon matrix. In some aspects, MMP2, MMP9, MMP14, or combinations thereof, are used to prepare decellularized tendon matrix compositions of the invention. The target cleavage sites for the MMP family, including MMP2, MMP9, and MMP14, have been mapped using a whole proteome approach by Eckhard et al., Data Brief 7: 299-310 (2017).

DTM Hydrogels

In another aspect, the present disclosure provides for decellularized tendon matrix hydrogels. Hydrogels may be produced using the intrinsic polymerization capability of pepsin-processed monomeric collagen by manipulating the temperature or pH. These approaches are well known, yet somewhat unpredictable, for example, Drake et al., Biochemistry 5:301-312 (1966) details the production of polymerizable proteolytic fragments of collagen. Other methods, such as those taught by Bahney et al., FASEB J, 25:1486-1496 (2011) and Ungerleider et al., Methods, 84:53-59 (2015), also well known. These well-known methods are particularly unpredictable when applied to protein-rich extracellular matrix tissues.

More reliable and better controlled crosslinking may be effected by using carbodiimide cross linker chemistry. In some embodiments, hydrogels are produced by mixing DTM compositions and reacting with a carboxyl-reactive cross linker, for example, 1-ethyl-3-(3-dimethylaminopropyl)carbodiimide, "EDC." EDC crosslinking is most efficient in acidic (e.g. about pH 4.5) conditions and best performed in buffers without extraneous carboxyls and amines. MES buffer (4-morpholinoethanesulfonic acid) is a suitable carbodiimide reaction buffer. Phosphate buffers and neutral pH (up to 7.2) conditions are compatible with the reaction chemistry, but with lower efficiency; increasing the amount of EDC in a reaction solution can readily compensate for any reduced efficiency. EDC is mixed 1:1 with N-hydroxysuccinimide (NHS) or its water-soluble analog (Sulfo-NHS) is to further improve crosslinking. EDC couples NHS to carboxyls, forming an NHS ester that is considerably more stable than the O-acylisourea intermediate while allowing for efficient conjugation to primary amines at physiologic pH.

In another aspect, a DTM hydrogel is formed by reconstituting DTM in a sterile pharmaceutically acceptable solution for injection.

Pharmaceutical Compositions for Injection

In one aspect, the invention provides a pharmaceutical composition for use in the repair or treatment of tendon tears. In a preferred embodiment, the invention provides pharmaceutical composition comprising a DTM hydrogel, that is applied directly to the location of tendon damage. In an aspect, the location of tendon damage is a first degree tear. In another aspect, the location of tendon damage is a second degree tear. In an aspect, the location of tendon damage is a third degree tear.

The pharmaceutical compositions are typically formulated to provide a therapeutically effective amount of a DTM hydrogel, the pharmaceutical composition further comprising one or more pharmaceutically acceptable excipients, carriers, including inert solid diluents and fillers, diluents, including sterile aqueous solution and various organic solvents, permeation enhancers, solubilizers and adjuvants.

In making the compositions of this disclosure, compositions comprising decellularized tendon matrix can also comprise an excipient. Some examples of suitable excipients include lactose, dextrose, sucrose, sorbitol, mannitol, starches, gum acacia, calcium phosphate, alginates, tragacanth, gelatin, calcium silicate, microcrystalline cellulose, PEG, polyvinylpyrrolidone, cellulose, water, sterile saline, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of an active ingredient (e.g., a growth factor) after implant into the patient by employing procedures known in the art.

In some cases, the pharmaceutical compositions described herein may comprise an excipient that can provide long term preservation, bulk up a formulation that contains potent active ingredients, facilitate drug absorption, reduce viscosity, add flavoring, or enhance the solubility of the pharmaceutical composition. Non-limiting examples of excipients can include anti-adherents, binders (e.g., sucrose, lactose, starches, cellulose, gelatin, or polyethylene glycol), coatings (e.g., hydroxypropyl methylcellulose or gelatin), disintegrants, glidants, lubricants, or preservatives (e.g., acids, esters, phenols, mercurial compounds, or ammonium compounds). A pharmaceutical composition of the present disclosure can comprise about 1%, 2%, 3%, 4%, 5%, 6%, 7%, 8%, 9%, 10%, 15%, 20%, 25%, 30%, 35%, 40%, 45%, 50%, or greater than about 50% of the excipient by weight or by volume. For example, a pharmaceutical composition can comprise 5% of an excipient by volume. In another example, a pharmaceutical composition can comprise 8% of an excipient by weight. It is contemplated that one or more vehicles may be chosen based on the active ingredient in the pharmaceutical composition.

In certain embodiments, a pharmaceutical composition of the present disclosure can comprise one or more solubilizers. As used herein, "solubilizers" include compounds such as triacetin, triethylcitrate, ethyl oleate, ethyl caprylate, sodium lauryl sulfate, sodium docusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrrns, ethanol, n-butanoL isopropyl alcohol, cholesterol, bile salts, polyethylene glycol 200-600, glycofurol, transcutol, propylene glycol, and dimethyl isosorbide and the like. A pharmaceutical composition of the present disclosure can comprise about 1%, 2%, 3%, 4%, 5%, 6%, 7%, 8%, 9%, 10%, 15%, 20%, 25%, 30%, 35%, 40%, 45%, 50%, or greater than about 50% of the solubilizer by weight or by volume. For example, a pharmaceutical composition can comprise 10% of a solubilizer by volume. In another example, a pharmaceutical composition can comprise 5% of a solubilizer by weight.

In some embodiments, the compositions comprise a stabilizing agent. In some embodiments, stabilizing agent is selected from, for example, fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. In some embodiments, amide analogues of stabilizers are also used. Other useful compositions include one or more antioxidants to enhance chemical stability where required. Suitable antioxidants include, by way of example only, ascorbic acid and sodium metabisulfite. In one embodiment, antioxidants are selected from metal chelating agents, thiol containing compounds and other general stabilizing agents.

Still other useful compositions include one or more surfactants to enhance physical stability or for other purposes. Suitable nonionic surfactants include polyoxyethylene fatty acid glycerides and vegetable oils, polyoxyethylene, hydrogenated castor oil, polyoxyethylene alkylethers, alkylphenyl ethers, octoxynol 10, and octoxynol 40.

In some embodiments, the compositions disclosed herein comprise preservatives.

Suitable preservatives for use in the compositions described herein include, but are not limited to benzoic acid, boric acid, p-hydroxybenzoates, phenols, chlorinated phenolic compounds, alcohols, quarternary compounds, quaternary ammonium compounds (e.g. benzalkonium chloride, cetyltrimethylammonium bromide or cetylpyridinium chloride), stabilized chlorine dioxide, mercurials (e.g. merfen or thiomersal), or mixtures thereof. In some embodiments, the preservative is methyl paraben. In some embodiments, the methyl paraben is at a concentration of about 0.05% to about 1.0%, about 0.1% to about 0.2% by weight or by volume.

In some embodiments, a composition of the present disclosure can comprise a base, and the base can include sodium stearyl fumarate, diethanolamine cetyl sulfate, isostearate, polyethoxylated castor oil, benzalkoniura chloride, nonoxyl 10, octoxynol 9, sodium lauryl sulfate, sorbitan esters (sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate, sorbitan tri-isostearate), lecithin, pharmaceutical acceptable salts thereof, combinations thereof, or derivatives thereof.

In an embodiment, the concentration of decellularized tendon matrix (DTM) in the DTM hydrogel pharmaceutical compositions is selected from the group consisting of about 0.2 mg/mL to 20 mg/mL; 0.2 mg/mL to 19 mg/mL; 0.2 mg/mL to 18 mg/mL; 0.2 mg/mL to 17 mg/mL; 0.2 mg/mL to 16 mg/mL; 0.2 mg/mL to 15 mg/mL; 0.2 mg/mL to 14 mg/mL; 0.2 mg/mL to 13 mg/mL; 0.2 mg/mL to 12 mg/mL; 0.2 mg/mL to 11 mg/mL; 0.2 mg/mL to 10 mg/mL; 0.2 mg/mL to 9 mg/mL; 0.2 mg/mL to 8 mg/mL; 0.2 mg/mL to 7 mg/mL; 0.2 mg/mL to 6 mg/mL; 0.3 mg/mL to 6 mg/mL; 0.4 mg/mL to 6 mg/mL; 0.5 mg/mL to 6 mg/mL; 0.6 mg/mL to 6 mg/mL; 0.7 mg/mL to 6 mg/mL; 0.8 mg/mL to 6 mg/mL; 0.9 mg/mL to 6 mg/mL; 1 mg/mL to 6 mg/mL; 2 mg/mL to 6 mg/mL; 3 mg/mL to 6 mg/mL; about 3 mg/mL; about 4 mg/mL; about 5 mg/mL; and about 6 mg/mL.

In an embodiment, the concentration of decellularized tendon matrix (DTM) in the DTM hydrogel pharmaceutical compositions is selected from the group consisting of about 1.0 mg/mL to 6 mg/mL; 1.1 mg/mL to 6 mg/mL; 1.2 mg/mL to 6 mg/mL; 1.3 mg/mL to 6 mg/mL; 1.4 mg/mL to 6 mg/mL; 1.5 mg/mL to 6 mg/mL; 1.6 mg/mL to 6 mg/mL; 1.7 mg/mL to 6 mg/mL; 1.8 mg/mL to 6 mg/mL; 1.9 mg/mL to 6 mg/mL; 2.0 mg/mL to 6 mg/mL; 2.1 mg/mL to 6 mg/mL; 2.2 mg/mL to 6 mg/mL; 2.3 mg/mL to 6 mg/mL; 2.4 mg/mL to 6 mg/mL; 2.5 mg/mL to 6 mg/mL; 2.6 mg/mL to 6 mg/mL; 2.7 mg/mL to 6 mg/mL; 2.8 mg/mL to 6 mg/mL; 2.9 mg/mL to 6 mg/mL; 3.0 mg/mL to 6 mg/mL; 3.1 mg/mL to 6 mg/mL; 3.2 mg/mL to 6 mg/mL; 3.3 mg/mL to 6 mg/mL; 3.4 mg/mL to 6 mg/mL; 3.5 mg/mL to 6 mg/mL; 3.6 mg/mL to 6 mg/mL; 3.7 mg/mL to 6 mg/mL; 3.8 mg/mL to 6 mg/mL; 3.9 mg/mL to 6 mg/mL; 4.0 mg/mL to 6 mg/mL; 4.1 mg/mL to 6 mg/mL; 4.2 mg/mL to 6 mg/mL; 4.3 mg/mL to 6 mg/mL; 4.4 mg/mL to 6 mg/mL; 4.5 mg/mL to 6 mg/mL; 4.6 mg/mL to 6 mg/mL; 4.7 mg/mL to 6 mg/mL; 4.8 mg/mL to 6 mg/mL; 4.9 mg/mL to 6 mg/mL; 5.0 mg/mL to 6 mg/mL; 5.1 mg/mL to 6 mg/mL; 5.2 mg/mL to 6 mg/mL; 5.3 mg/mL to 6 mg/mL; 5.4 mg/mL to 6 mg/mL; 5.5 mg/mL to 6 mg/mL; 5.6 mg/mL to 6 mg/mL; 5.7 mg/mL to 6 mg/mL; 5.8 mg/mL to 6 mg/mL; and 6 mg/mL.

In an embodiment, the DTM hydrogel percentage (%) in the pharmaceutical composition is selected from the group consisting of about provided in the pharmaceutical compositions of the invention is independently less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, suspending agents, binders, fillers, plasticizers, lubricants, and mixtures thereof.

Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, and thimerosal.

The composition can further comprise a peptide. The composition can further comprise a protein. The composition can further comprise an amino acid. The composition can further comprise water.

The composition can further comprise at least one growth factor. In some cases, the at least one growth factor can comprise insulin-like growth factor-1, insulin-like growth factor binding protein-3, vascular endothelial growth factor (VEGF), hepatocyte growth factor (HGF), placenta growth factor (PLGF), or any combination thereof. The at least one growth factors can enhance viability, enhance stability of product, differentiation of cells, preservation of sternness, reduce anti-inflammatory, or any combinations thereof. The at least one growth factor can be added to the composition. The at least one growth factor can be added to a subcomponent of the composition. The at least one growth factor can be added to a viscosity modifying component, a plurality of isolated stem cells, an isolated inductive component, an isolated scaffolding component, or any combinations thereof. For example, the at least one growth factor can be added to a composition of the present disclosure comprising a decellularized tendon matrix to enhance host tissue integration with the composition upon transplant into a host. The at least one growth factor can be added prior to forming the composition. The at least one growth factor can be added after forming the composition.

The composition can further comprise at least one of: chemokine ligand 2, macrophage inflammatory protein-1 (MIP-1) alpha, MIP-1 beta, MIP-2, beta-chemokine ligand-5, beta-chemokine ligand-20, alpha-chemokine ligand-14, lipopolysaccharide-induced alpha-chemokine, Granulocyte-macrophage colony-stimulating factor, interleukin IL-1 beta, phorbol myristate acetate, epidermal growth factor, fibroblast growth factor, vascular endothelial growth factor, connective tissue growth factor, platelet-derived growth factor, insulin-like growth factor, nerve growth factor, hepatocyte growth factor, colony-stimulating factor, stem cell factor, keratinocyte growth factor, granulocyte colony-stimulating factor, granulocyte macrophage colony-stimulating factor, glial derived neurotrophic factor, ciliary neurotrophic factor, endothelial-monocyte activating polypeptide, epithelial neutrophil activating peptide, erythropoietin, bone morphogenetic protein, brain-derived neurotrophic factor, transforming growth factor beta, tumor necrosis factor, or any combination thereof. The composition can further comprise at least one hormone. In some cases, the at least one hormone can be prolactin or leptin.

In some cases, there can be six major growth factor families (EGF, FGF, IGF, PDGF, TGF, and VEGF) associated with healing. Examples of such growth factors can include, but are not limited to, platelet derived growth factor (PDGF-A, PDGF-B, PDGF-C, and PDGF-D), insulin-like growth factor I and II (IGF-I and IGF-II), acidic and basic fibroblast growth factor (aFGF and bFGF), alpha and beta transforming growth factor (TGF-a and TGF-β (for example, TGF-beta 1, TGF beta 2, TGF beta 3)), epidermal growth factor (EGF), and others. These growth factors can stimulate mitosis of one or more of the cells involved in healing and can be combined.

Other positive angiogenesis agents co-administered with the compositions disclosed herein can include, but are not limited to, e.g., HGF, TNF-α, angiogenin, IL-8, etc. Still further examples of additional agents can include Platelet-derived growth factor (PDGF) (e.g., Becaplermin (rhPDGF-BB) such as REGRANEX®, adenosine-A2A receptor agonists;

keratinocyte growth factor (KGF-2, repifermin; lactoferrin (LF); thymosine beta-4 (T134); thrombin-derived activating receptor peptide (TP508; CHRYSALIN®; adenoviral vector encoding platelet-derived growth factor (PDGF-B); autologous bone marrow stem cells (BMSC); and, engineered living tissue grafts (e.g., Apligraf, etc.). Antibiotic and antiseptic ulcer agents can also be combined. Immunosuppressive treatment (e.g., corticosteroids, radiation therapy, chemotherapy) can be combined with the compositions disclosed herein.

A person having skill in the art will appreciate that additional agents can be co-administered with the composition disclosed herein or administered separately.

Compositions of the invention can comprise, in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above.

Other Pharmaceutical Compositions

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, et al., eds., Handbook of Clinical Drug Data, Tenth Edition, McGraw-Hill, 2002; and Pratt and Taylor, eds., Principles of Drug Action, Third Edition, Churchill Livingston, N.Y., 1990, each of which is incorporated by reference herein in its entirety.

The compositions of the invention may also be delivered via an impregnated or coated device such as a suture, for example, suture anchor. Such a method of administration may, for example, aid in the prevention or amelioration of tendon damage or injury. A composition of the invention may be administered, for example, by local delivery from the suture or suture anchor. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly(ether-ester) copolymers (e.g., PEO-PLLA); polydimethylsiloxane, poly(ethylene-vinylacetate), acrylate-based polymers or copolymers (e.g., polyhydroxyethyl methylmethacrylate, polyvinyl pyrrolidinone), fluorinated polymers such as polytetrafluoroethylene and cellulose esters; and Polyether ether ketone (PEEK). Metals or biocomposite materials, for example poly(lactic acid) (PLA) and beta-tricalcium phosphate ((3-TCP) are also suitable. PLA/hydroxyapatite may also be used, see, e.g. Dorozhkin, Biomatter, 1:3-56 (2011). Suitable matrices may be nondegrading or may degrade with time, releasing the compound or compounds. Compositions of the invention may be applied directly to the sites of tendon injury and/or directly to sites of tendon damage. In some aspects, compositions of the invention are applied adjacent to sites of tendon injury and/or adjacent to sites of tendon damage. In another aspect, compositions of the inventions are applied to tendons in need of regeneration.

DTM hydrogels may be applied to the surface of the suture, suture anchor, or medical device by various methods such as dip/spin coating, spray coating, dip-coating, and/or brush-coating. The compounds may be applied in a solvent and the solvent may be allowed to evaporate, thus forming a layer of hydrogel onto the suture, suture anchor, or medical device. Alternatively, the compound may be located in the body of the suture, suture anchor, or medical device, for example in microchannels or micropores. When implanted, the compound diffuses out of the body of the suture, suture anchor, or medical device to contact the tendon. Such suture, suture anchor, or medical devices may be prepared by dipping a suture, suture anchor, or medical device manufactured to contain such micropores or microchannels into a solution of the compositions of the invention in a suitable solvent, followed by evaporation of the solvent. Excess hydrogel on the surface of the suture, suture anchor, or medical device may be removed via an additional brief solvent wash. In yet other embodiments, compounds of the invention may be covalently linked to a suture, suture anchor, or medical device. A covalent linker may be used which degrades in vivo, leading to the release of the compound of the invention. Any bio-labile linkage may be used for such a purpose, such as ester, amide or anhydride linkages.

In some aspects, DTM hydrogels of the invention are directly applied to a tendon. In some aspects, DTM hydrogels of the invention are directly applied to a tendon using a surgical or medical needle ranging from a 10-gauge needle to a 25-gauge needle. The needle can be 10-gauge, 11-gauge, 12-gauge, 13-gauge, 14-gauge, 15-gauge, 16-gauge, 18-gauge, 20-gauge, 22-gauge, 23-gauge, 24-gauge, or 25-gauge. In some aspects, the needle is 16-gauge to 20-gauge. The viscosity of the DTM hydrogel may be modulated to optimize the composition for delivery through a particular gauge needle; for example, 16-gauge or 20-gauge.

The rheological properties of the DTM hydrogels of the invention may be matched to a particular medical or surgical needle gauge for optimal injection. For example, the dynamic viscosity of the DTM hydrogels of the invention are between about 0.05 Pa*s to about 1.0 Pa*s.

The invention also provides kits. The kits comprise lyophilized DTM composition, and carbodiimide crosslinking reagents, either alone or in combination in suitable packaging, and written material that can include instructions for use, discussion of clinical studies and listing of side effects. In some embodiments, the kit further comprises an applicator for applying the composition to a tendon in need thereof. In some embodiments, the kit further comprises a removable attachment enabling mixing. In an aspect the kit comprises a syringe with lyophilized DTM, a second syringe with an aqueous resuspension buffer, and a mixing connector, that connects the syringes allowing mixing between the two syringes. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials.

Methods of Treating Tendons

In an aspect, compositions of the invention are used to stimulate tendon regeneration, the method comprising: (i) resuspending a DTM composition according to the present invention in a pharmaceutically acceptable carrier; and (ii) applying the resuspended DTM composition to a tendon site in need of stimulating tendon regeneration.

In another aspect, a DTM hydrogel is prepared immediately before treating a subject in need thereof, the method comprising: (i) resuspending a DTM composition according to the present invention in a pharmaceutically acceptable carrier; (ii) preparing a DTM hydrogel; and (iii) applying the DTM hydrogel to a tendon site in need of stimulating tendon regeneration. In some aspects, the tendon site in need of stimulating tendon regeneration is a first degree tear. In some aspects, the tendon site in need of stimulating tendon regeneration is a second degree tear; in another aspect, the tendon site in need of stimulating tendon regeneration is a third degree tear. In some aspect, the site is a complete tear.

In some aspects, the tendon site in need of stimulating tendon regeneration is a site with an acute injury. In some aspects, the tendon site in need of stimulating tendon regeneration is selected from the group consisting of lateral epicondylitis, Achilles tendonitis, peroneal tendonitis, patellar, quadriceps tendonitis and combinations thereof.

In some aspects, the DTM hydrogel is prepared using carbodiimide chemistry. In some aspects, the DTM hydrogel is prepared by reconstituting the DTM in a pharmaceutically acceptable sterile solution for injection.

In an aspect, DTM compositions of the invention are applied to a tendon site in need of repair by single needle injection. In an aspect, application of DTM compositions of the invention is image guided. In some aspects, DTM compositions of the invention are applied to a tendon site in need of repair using arthroscopy. In another aspect, DTM compositions of the invention are applied to a tendon site in need of repair directly, in the course of an open surgical procedure.

In some aspects, compositions of the invention are administered to one or more joints via image guided injection. X-ray, computed tomography (CT), or ultrasound are useful imaging methods for guiding joint injections.

Although the present invention has been described in considerable detail with reference to various versions thereof, other versions are possible. Therefore, the spirit and scope of the appended claims should not be limited to the description of the preferred versions contained herein.

The reader's attention is directed to all papers and documents which are filed concurrently with this specification and which are open to public inspection with this specification, and the contents or all such papers and documents are incorporated by reference herein. All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is only one example of a generic series of equivalent or similar features.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1 Preparation of Decellularized Tendon Matrix

A human cadaveric Achilles tendon is washed with phosphate buffered saline (PBS), pH. 7.4, then the sheath, adipose and synovial tissue is removed from tendon tissue specimen. The tendon tissue specimen is then minced into pieces roughly 1 to 4 $mm^3$ in size, then washed with phosphate-buffered saline (PBS).

The minced tendon pieces are immersed in decellularization solution, comprising 1% w/v sodium dodecyl sulfate (SDS), and moderately agitated. The minced material is carefully washed multiple exchanges of ultrapure water to remove residual SDS and cellular components.

The material is then flash frozen then milled yielding a heterogeneous material with a range of particle sizes. The resulting material is then resuspended in MMP digestion buffer. This suspension is incubated.

Stop solution is then added to halt MMP digestion; the buffer is then changed and neutralization solution. The material is then washed with multiple buffer exchanges of wash buffer, and then lyophilized.

Decellularization is assayed by comparing SYTO Green 11 (nuclear) staining of native tendon starting material to the final DTM product. Decellularization is further confirmed using Hematoxylin & Eosin, 4',6-diamidino-2-phenylindole (DAPI) staining, agarose gel electrophoresis, and quantification of remnant DNA. The DTM product is substantially free of nuclear staining. Remnant DNA is present at or below about 2 ng/mL.

MALDI-TOF mass spectrometry is used to demonstrate the presence of TGF-β in the DTM product.

Example 2 Characterization of DTM Hydrogels

A DTM hydrogel is prepared by resuspending a DTM of the invention in a pharmaceutically acceptable sterile solution for injection. Then the following methods, according to Zuidema et al., J. Biomed. Mater. Res. B Appl. Biomater., 102:1063-73 (2014) are used to characterize the resulting DTM hydrogel: (1) Time sweep to determine the gelation time of the hydrogel. (2) Strain sweep to determine the linear-viscoelastic region of the hydrogel with respect to strain. (3) Frequency sweep to determine the linear equilibrium modulus plateau of the hydrogel. (4) Time sweep with values obtained from strain and frequency sweeps to accurately report the equilibrium moduli and gelation time.

Example 3 DTM Processing for Maintaining a Native Growth Factor Profile

Decellularization and enzymatic processing techniques were developed to generate a decellularized tendon matrix putty that preserves TGF-β bioactivity in order to promote tissue regeneration.

Tendons have a poor regenerative capacity and typically heal through scarring rather than with a native-like tissue structure resulting in diminished mechanical strength. As a consequence, tendon repairs, such as rotator cuff repairs, have failure rates ranging from 20 to 90% depending on patient age, tear size and other biological factors. There is an unmet clinical need to stimulate tendon healing to produce a stronger regenerate in order to improve patient outcomes.

Decellularized extracellular matrix (ECM) have been frequently utilized as a regenerative material for tissue engineering as it retains proteins and growth factors native to the tissue and also can provide structural support. There are multiple growth factors which drive tendon remodeling, specifically transforming growth factor beta (TGF-β), has been studied for its role in regenerative healing. It has been shown that TGF-β signaling is critical in the formation of tendons during development. Following injury, TGF-β is temporally regulated to promote healing by stimulating collagen production and angiogenesis. Furthermore, exogenous TGF-01 injections were reported to increase collagen type I and III mRNA and an increase in biomechanical function of the repaired tendons was also found in this group.

Objectives—(i) To develop a decellularization technique, (ii) To develop a method for enzymatically digesting decellularized tendons, and (iii) To characterize the protein profile of decellularized tendon matrix (DTM).

Native Tendon Characterization—The goal was to determine which tendons were best to develop an allograft product. Patella and Achilles tendons were characterized for DNA content and native protein concentrations. Any differences between location and protein profile within each source (i.e. proximal vs. distal) was also determined. As shown in FIGS. 1A-B and 2A-B, no significant difference between patella and Achilles tendons was found. DNA content was measured using DNEasy kits (Qiagen). Total protein content was measured using a BCA kit (Thermo Scientific). As TGF-β is a pivotal growth factor in tendon healing, it is important to determine preprocessed (native) TGF-β concentrations within each tendon (patella vs. Achilles) and its location (proximal, mid, distal) (see, e.g., FIGS. 2A-B).

Figure 1B:
FIGS. 1A-B illustrate native tendon characterization of DNA content (FIG. 1A) and protein content (FIG. 1B) in tendon prior to processing native patella and Achilles tendons. Measurements depict tendons from a total of 6 donors.
Figure 1B:
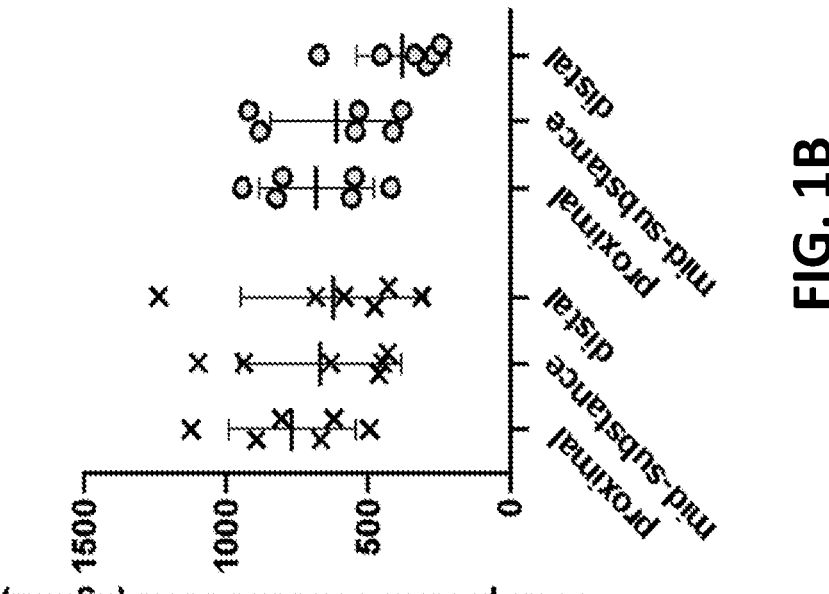
Figure 1A:
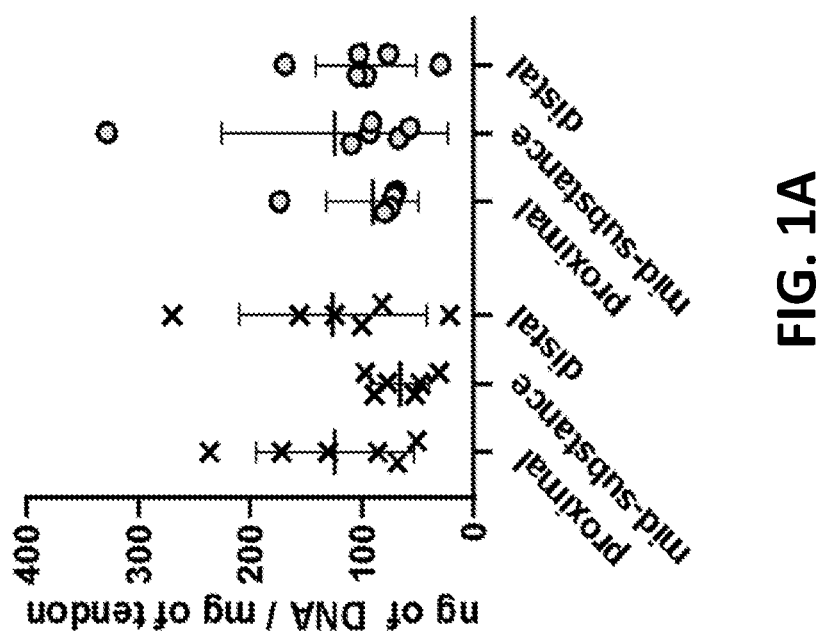
Figures 2A, 2B:
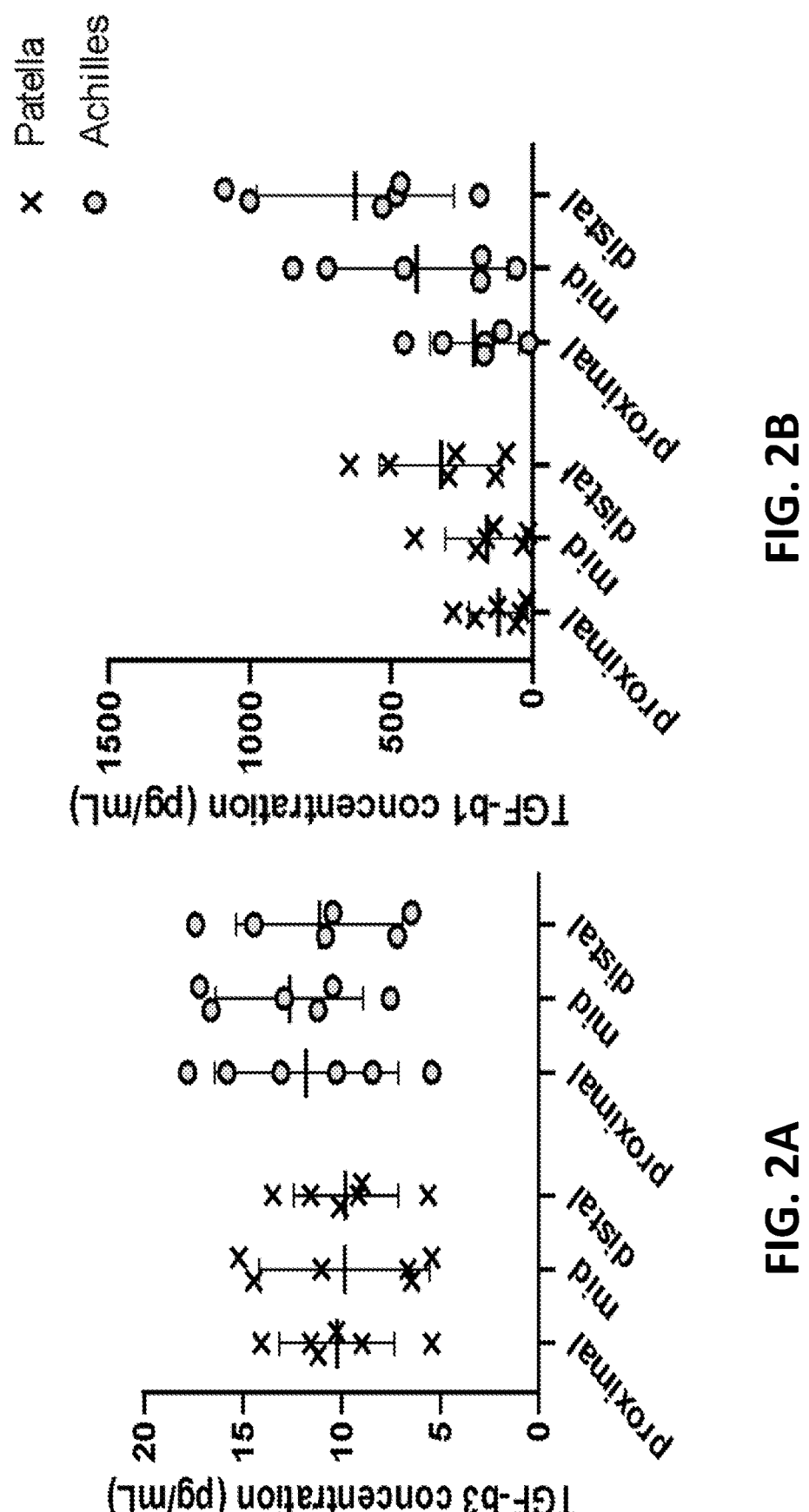
FIGS. 2A-B illustrate native TGF-β concentrations based on tendon type and location. TGF-β3 concentration (FIG. 2A) and TGF-β1 concentration (FIG. 2B) found in native tendon samples (prior to processing) are shown.
Figure 3:
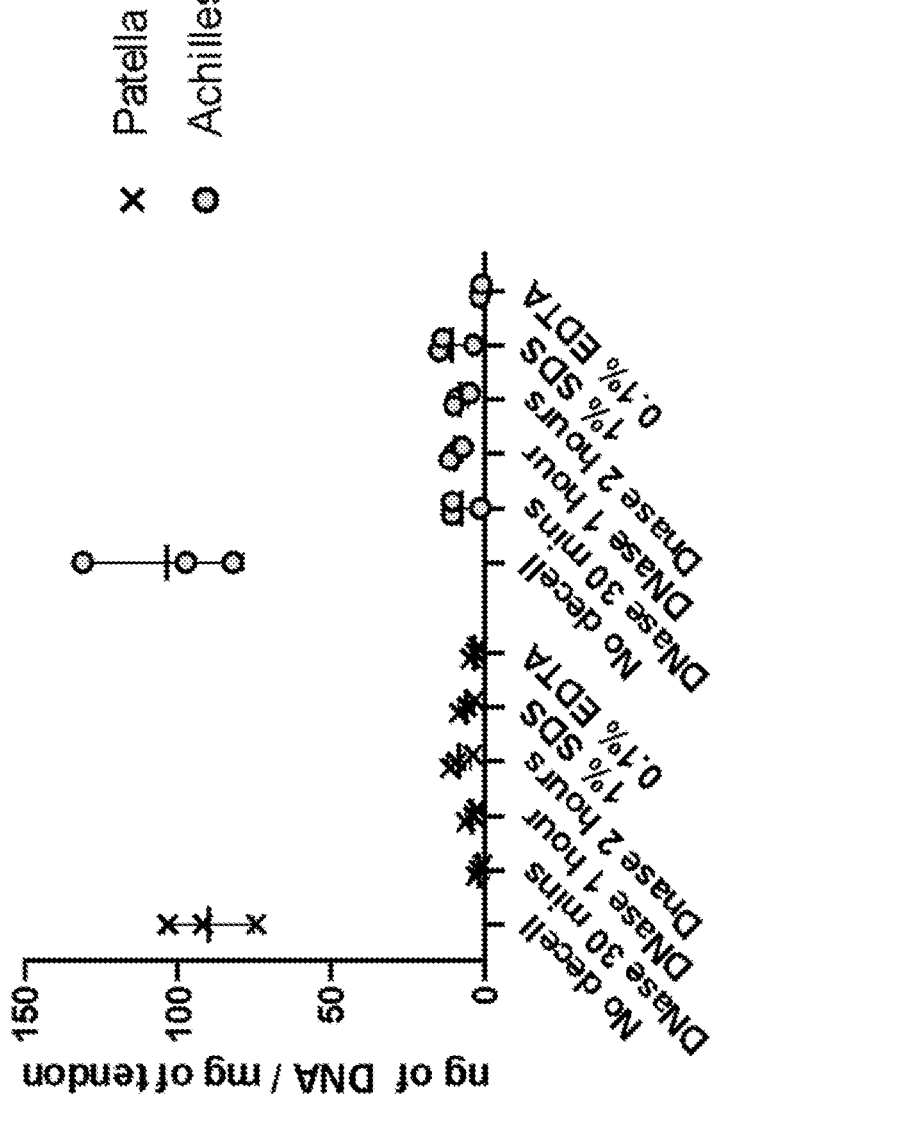
FIG. 3 illustrates a comparison of decellularization using DNase and detergents. DNA content in both patella and Achilles tendons is measured in native tendon, tendon treated with DNase 50U for 1 hour, tendon treated with DNase 50U for 2 hours, and tendons treated with traditional decellularization methods using SDS or EDTA.

Detergent-free Decellularization—The aim of the study was to develop a gentler and faster method of decellularization compared to traditional detergent-based method. DNase was compared to detergents, such as SDS and EDTA, which often have long processing times (1-2 weeks). Different time and concentrations of DNase were tested. As shown in FIG. 3, it was determined that 1 hour of decell with DNase 50U was significantly different than the native DNA content and was shown to be equivalent to traditional methods.

Figure 4:
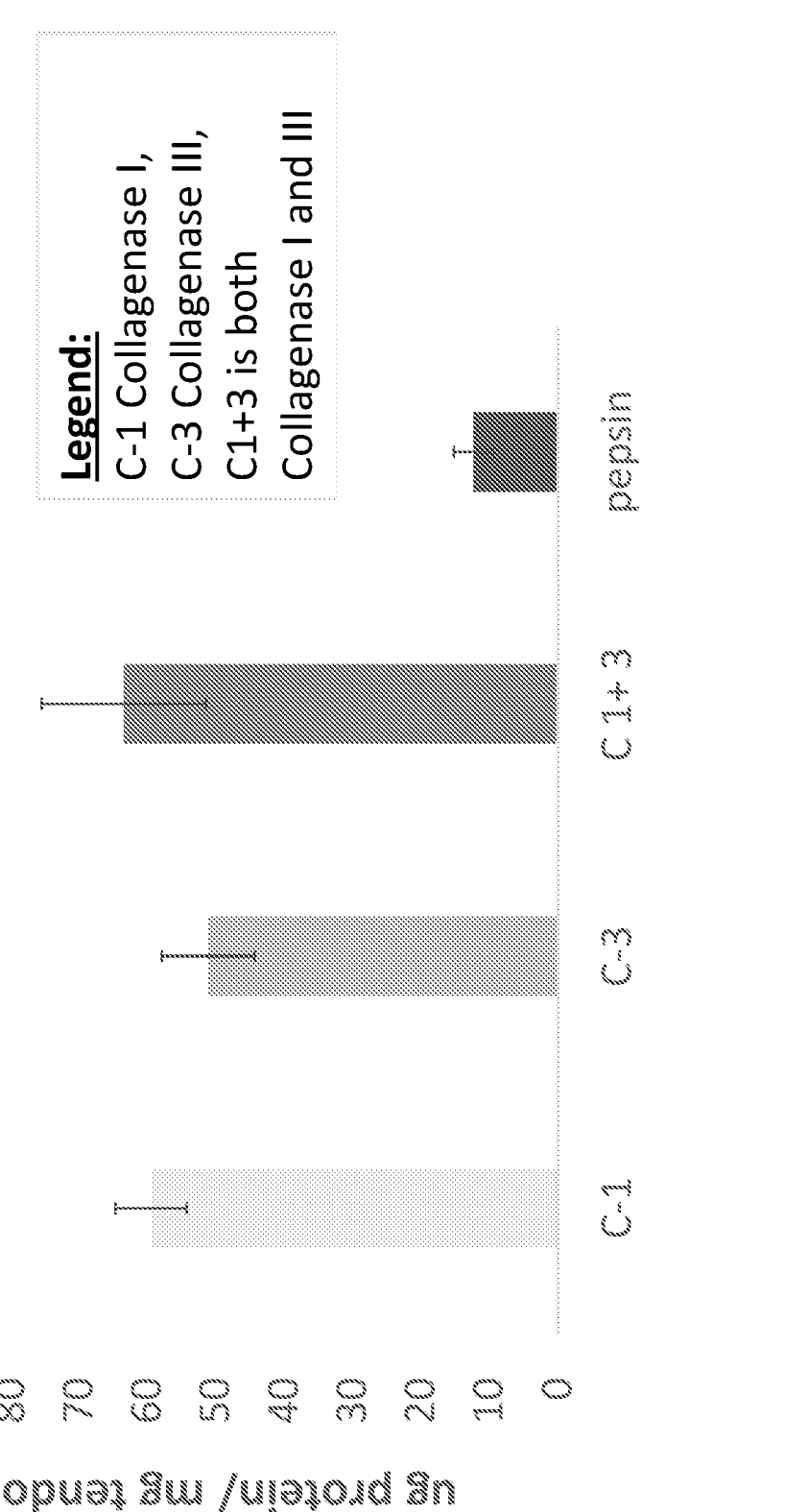
FIG. 4 illustrates total protein of tendons using various enzymatic reagents to digest the tendon samples, including C-1 Collagenase I, C-3 Collagenase III, both C-1 Collagenase I and C-3 Collagenase III, and pepsin.
Figure 5:
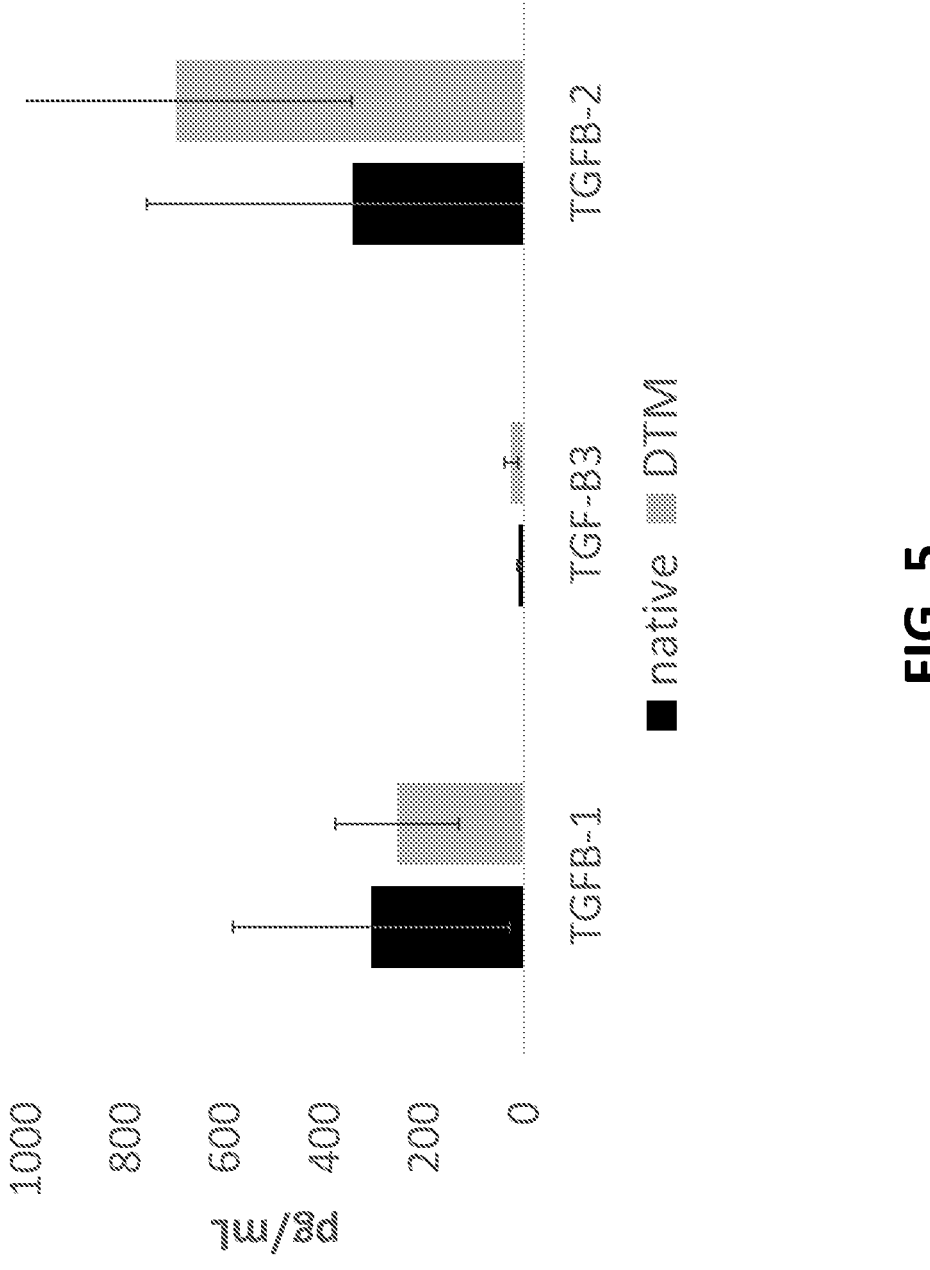
FIG. 5 illustrates TGF-β concentrations before and after processing tendon into decellularized tendon matrix. Native tendon is measured by averaging all proximal, mid-substance and distal portions of both patella and Achilles tendons.
Figure 6B:
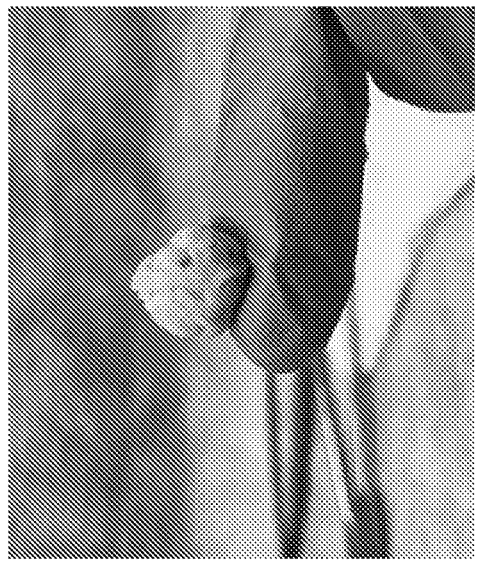
FIGS. 6A-B illustrate that decellularized tendon matrix processing facilitates an elastic characteristic which has the capacity to stretch (FIG. 6A) from an unstretched conformation (FIG. 6B) without being pulled apart. DTM is storage stable as a sterile lyophilized powder and can be reconstituted into a putty or an injectable solution. This image shows the DTM putty which can be formed by resuspending the lyophilized DTM with 3-5 ul/mg. This putty is moldable/stretchable for surgical application to the desired region of repair.
Figure 6A:
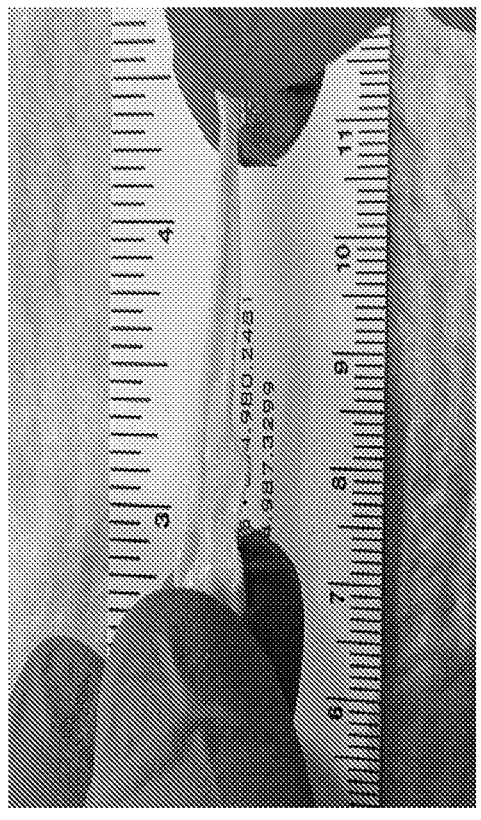

Collagenase Digestion Maximizes Protein Content—Enzymatic digestion allows for decellularized tendons to be manipulated into surgical friendly forms, such as an injectable system or a putty. Enzymatic digestion was modified in order to maximize functionality of growth factors. As shown in FIG. 4, collagenase I, III and a combination of the two were compared to pepsin digestion. All tendon samples were measured in μg total protein per mg tissue (μg protein/mg tissue). To make the enzymatic solutions, collagenase I (Life Technologies) was used at 2 mg/1 mL PBS, collagenase III (MP Biomedicals) at 1 mg/1 mL PBS and pepsin (Sigma) at 1 mg/1 mL 0.1 M HCl. All samples were incubated for 24 hours. Decellularized Tendon Matrix (DTM) Maintains TGF-β Proteins—To ensure that our decellularized tendon matrix (DTM) maintained bioactivity, TGF-β levels of the native tissue were compared to the processed product. TGFβ I, II and III all play an important role in tendon healing and repair. Following enzymatic digestion and a final lyophilization step, 30 μg of total protein was measured per sample based on the BCA results. A TGF-β Milliplex kit (Millipore Sigma) was utilized for measurement of all DTM samples. As shown in FIG. 5, The final prototype of DTM retains TGFβ I, II and III. As shown in FIGS. 6A-B, DTM processing facilitates an elastic characteristic which has the capacity to stretch (FIG. 6A) without being pulled apart.

There is an unmet clinical need to stimulate tendon healing to produce a stronger regenerate in order to improve patient outcomes. Current standard of care in tendon repair has high failure rates due in part to excessive scarring leading to reduced biomechanical functionality of the joint. In this study, a technique to generate a decellularized tendon matrix putty that preserves TGF-β bioactivity in order to promote tissue regeneration has been developed. Additional testing is being done, such as in vitro assays focused on cellular response to the DTM and an in vivo rotator cuff repair model to further characterize DTM efficacy in promoting tendon repair.

Example 4 Tendon Decellularization, & Enzymatic Digestion and Reconstitution of Decellularized Tendon Matrix (DTM)

The aim was to develop a gentler and faster method of decellularization compared to traditional detergent-based method. DNase was compared to detergents, such as SDS and EDTA, which often have long processing times (1-2 weeks). Different time and concentrations of DNase were tested. It was determined that 1 hour of decell with DNase 50U was significantly different than the native DNA content and was shown to be equivalent to traditional methods. DTM was prepared according to the following procedure.

Method of Tendon Decellularization—First, the tendon is weighed and recorded. Next, the tendon is minced into homogenously sized, smaller pieces. Next, to decellularized, the minced pieces are placed in DNase solution (see, e.g., table below; at 0.5 g tendon/mL DNase solution; DNase solution: 50 U DNase I per 1 mL 1×PBS; for 2 gram minced tendon, place in 4 mL 1×PBS and add 200 U DNase). Next, incubate at 56° C. for 1 hour with moderate shaking. Next, to wash the DTM, add 1×PBS at twice the initial volume (if 1 mL DNase solution was added, add 2 mL of 1×PBS). Next, place the DTM on 70 um cell strainers and centrifuge at 2000 G for 5-10 mins. Finally, freeze at −80° C. for at least 30 minutes, and place the tube in lyophilizer.

| | Putty | Injectable |
|---|---|---|
| Broad Range | .02-.25 g tendon/mL collagenase solution | .02-.25 g tendon/mL collagenase solution |
| Optimal Range | .10-.20 g tendon/mL collagenase solution | .02-.1 g tendon/ collagenase solution |

Enzymatic Digestion (Injectable DTM)—First, the decellularized tendon is weighed and recorded. Next, To create an injectable, weigh out 0.02-0.10 g tendon and add 1 mL collagenase solution (Collagenase type I @ 2 mg/mL, Collagenase type III @ 1 mg/mL in 1×PBS). Next, incubate at 37° C. for 24 hours. Next, to wash the DTM, add 1×PBS at twice the initial volume (if 1 mL collagenase solution was added, add 2 mL of 1×PBS). Next, place the DTM on 70 um cell strainers and centrifuge at 2000 G for 5-10 mins. Next, place the DTM into a new microcentrifuge tube with 1 mL of PBS, and vortex for 30 sec. Next, place this solution into a 100 KDa filter, and spin at 12,000 G for 5 mins. Finally, freeze at −80° C. for at least 30 minutes, and place the tube in lyophilizer.

Enzymatic Digestion (Putty DTM)—First, the decellularized tendon is weighed and recorded. Next, To create a putty, weigh out 0.10-0.20 g tendon and add 1 mL collagenase solution (Collagenase type I @ 2 mg/mL, Collagenase type III @ 1 mg/mL in 1×PBS). Next, incubate at 37° C. for 12 hours. Next, to wash the DTM, add 1×PBS at twice the initial volume (if 1 mL collagenase solution was added, add 2 mL of 1×PBS). Next, place the DTM on 70 um cell strainers and centrifuge at 2000 G for 5-10 mins. Next, place the DTM into a new microcentrifuge tube with 1 mL of PBS, and vortex for 30 sec. Next, place this solution into a 100 KDa filter, and spin at 12,000 G for 5 mins. Finally, freeze at −80° C. for at least 30 minutes, and lyophilize.

Reconstitution—Add 2-5 uL of 1×PBS/mg tendon, and add additional PBS can be added until you reach desired consistency.

Figure 7:
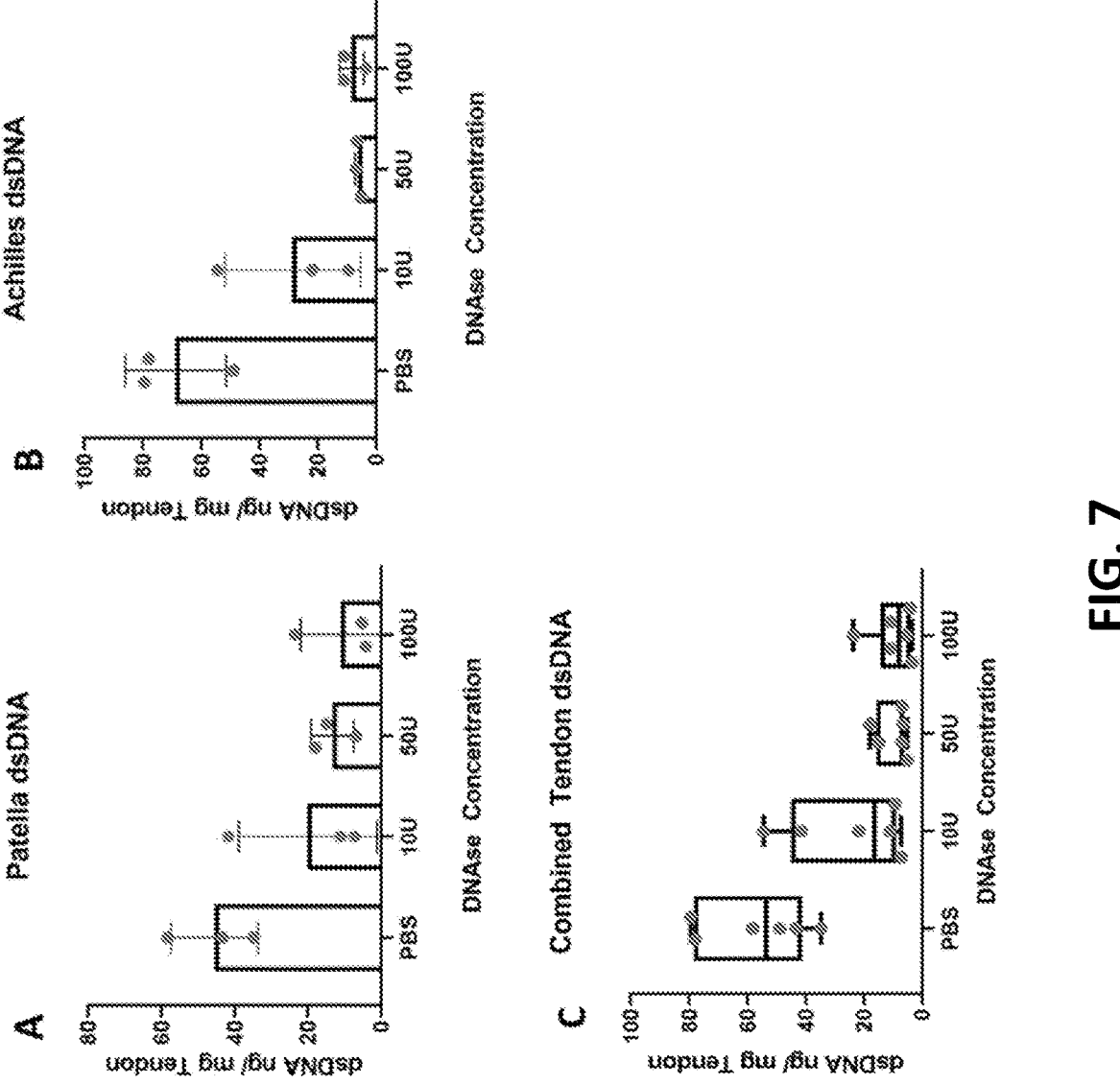
FIGS. 7A-C illustrate that DNAse treatment effectively decellularizes tendon tissue. Tendon was decellularized using various concentrations of DNAse (10U, 50U, and 100U) over 1 hour. 1×PBS was used as a control for no decellularization. DNA concentration was determined using DNEasy kits (Qiagen). This data shows that as little as 50U of DNAse is effective in decellularizing tissue.
Figure 8:
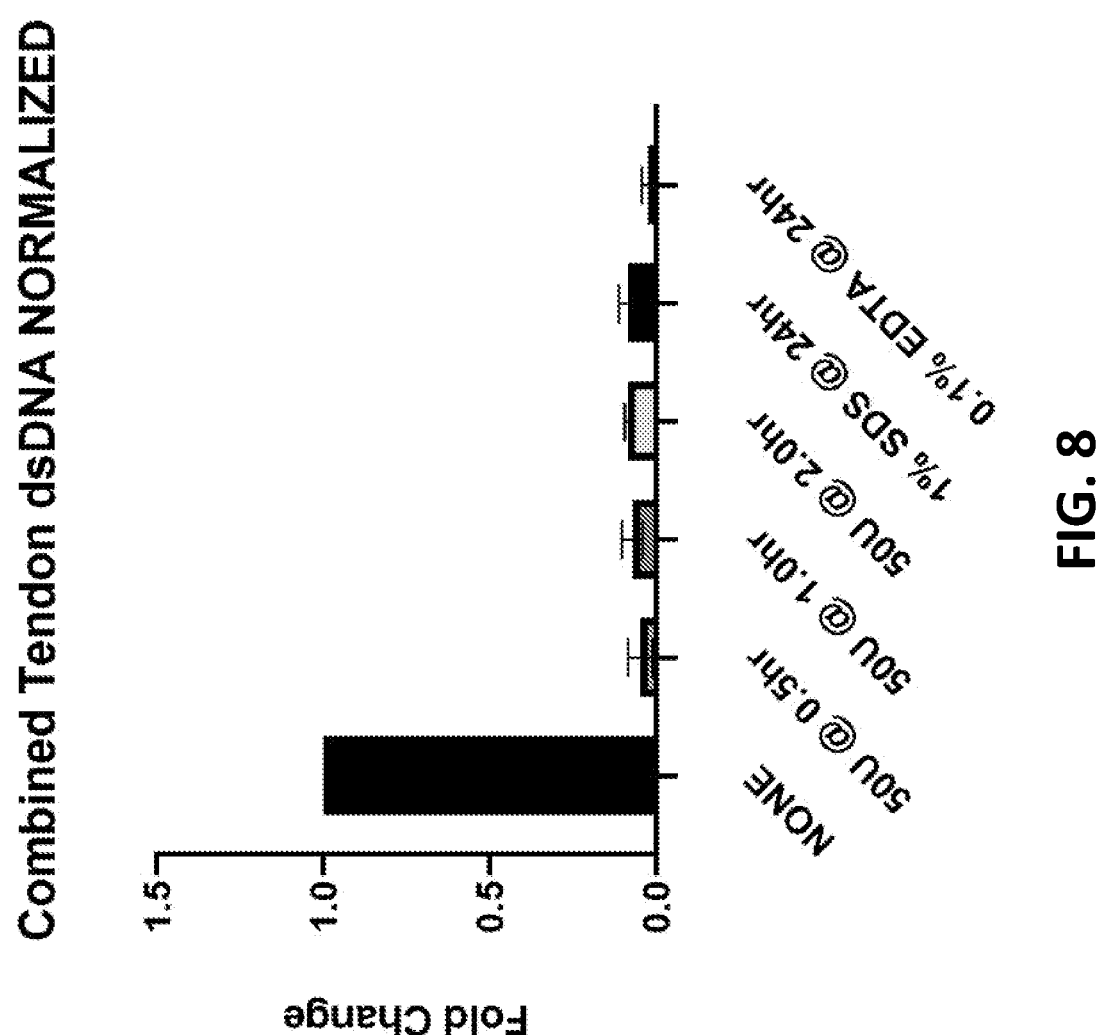
FIG. 8 illustrates that DNAse treatment is as effective as standard detergent methods at decellularizing tendon. DNAse at 50U was compared to traditional detergents, 1% SDS and 0.1% EDTA. DNAse 50U was tested at 0.5 hours.
Figure 9:
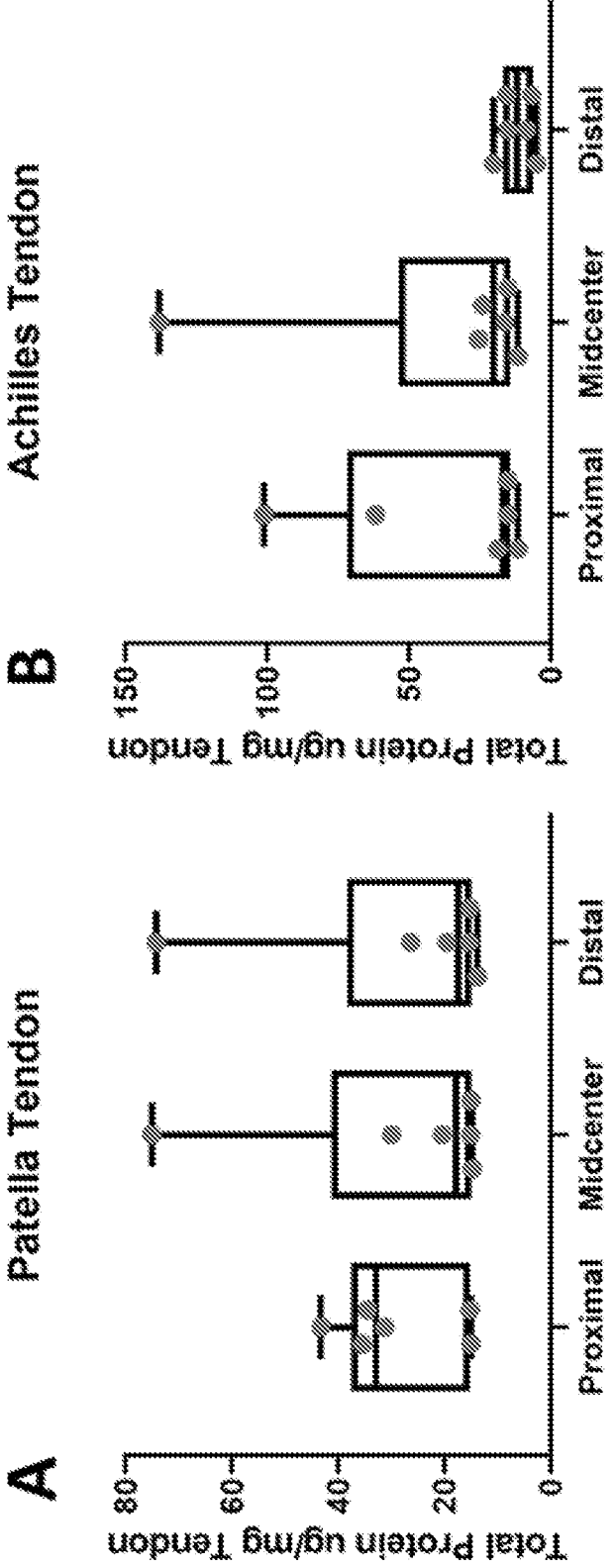
Figure 9:
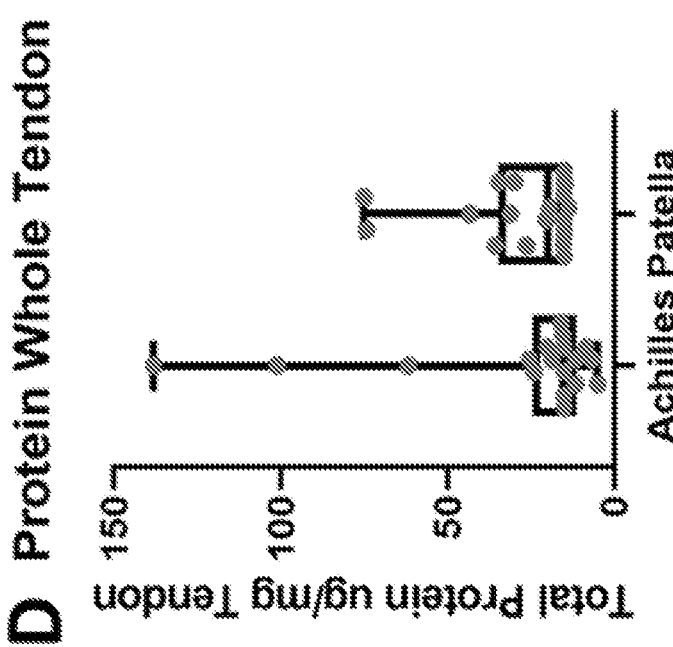
Figure 9:
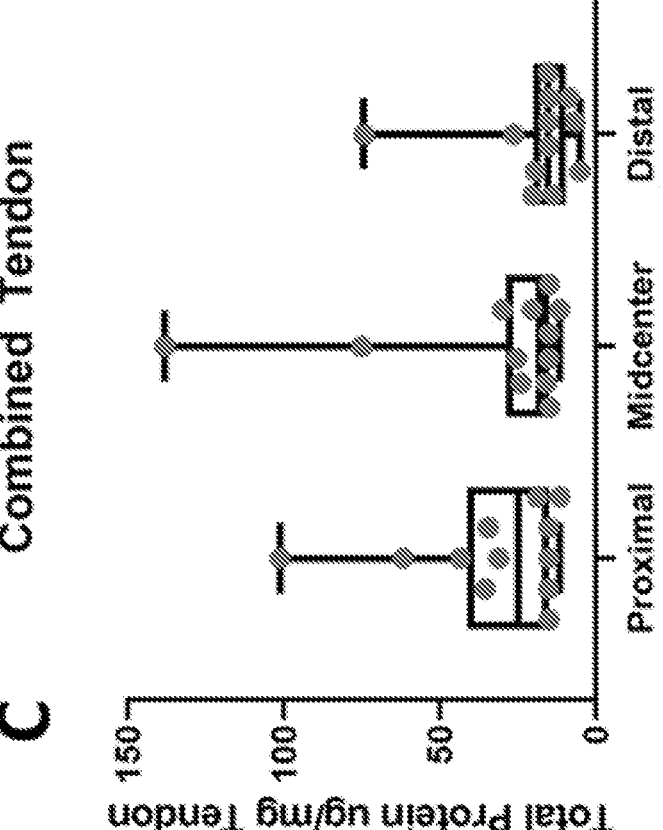
Figure 9:
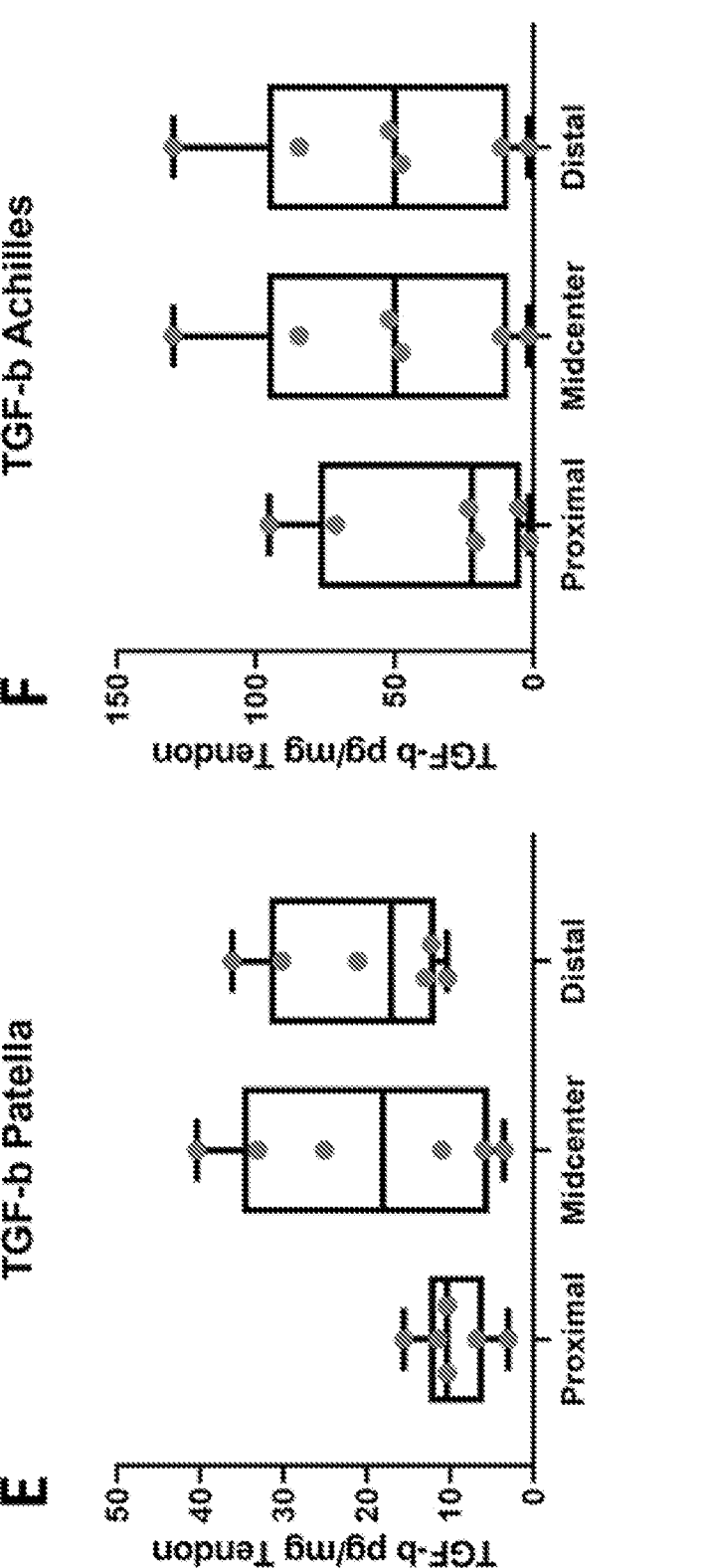
Figure 9:
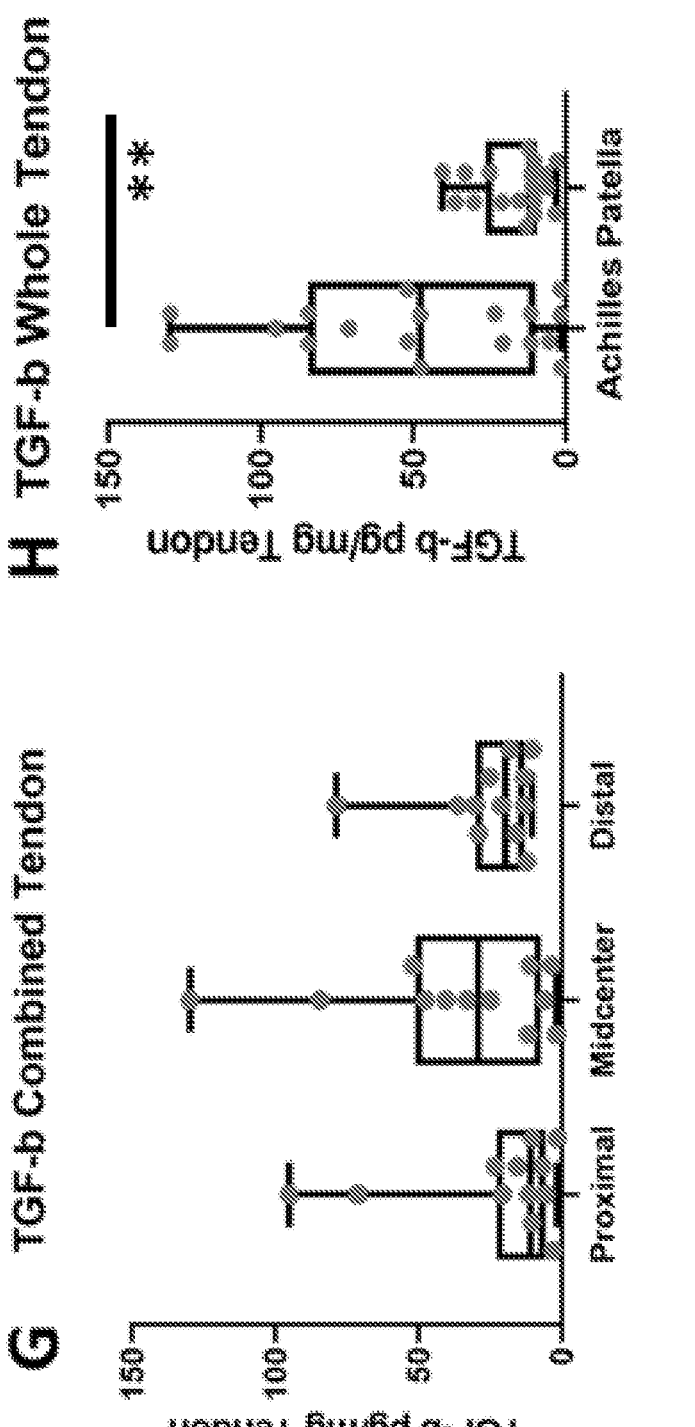

Tendon was decellularized using various concentrations of DNAse (10U, 50U, and 100U) over 1 hour (see, e.g., FIG. 7). 1×PBS was used as a control for no decellularization. DNA concentration was determined using DNEasy kits (Qiagen). This data shows that as little as 50U of DNAse is effective in decellularizing tissue. As shown in FIG. 8, DNAse at 50U was compared to traditional detergents, 1% SDS and 0.1% EDTA. DNAse 50U was tested at 0.5 hours, 1 hours, and 2 hours, while standard SDS and EDTA protocol calls for a 24-hour decellularization. DNA concentration was determined using DNEasy kits (Qiagen, n=3). All values were normalized to no decellularization. Tukey's HSD multiple comparison post-hoc testing shows no significant difference between the different times of DNAse treatment or decellularization by DNAse versus SDS and EDTA. Also shown in the following table, is the percent DNA left in Patella and Achilles tendons following various decell methods, and/or different time periods:

| | no decell | DNAse 30 mins | DNAse 1 hr | DNAse 2 hr | 1% SDS | 0.1% EDTA |
|---|---|---|---|---|---|---|
| Avg % DNA left | 100.00% | 5.07% | 7.32% | 8.60% | 8.70% | 2.61% |
| % Range DNA left | 2-8% | 4-10% | 7-9% | 6-12% | 1-3% | |

Native tendon was characterized to determine which tendons were best to develop an allograft product. Patella and Achilles tendons were characterized for DNA content and native protein concentrations. We also aimed to determine any difference between location and protein profile within each source (i.e. proximal vs. distal). No significant difference was found in total protein or TGFβ content between the different regions of the tendon. However, we did find that Achilles has a higher relative content of protein. The Achilles and Patellar tendons were divided into ⅓ sections consisting of the proximal, midcenter/middle, and distal ends of the tendon. (FIG. 9A-D) Total protein of the native tendons was measured using a BCA protein quanti-fication kit (Thermo Scientific). (FIG. 9E-H) TGF-β was measured using a TGF-β magnetic bead panel Milliplex kit (Millipore Sigma, #TGFBMAG-64K-03). ANOVA shows no statistically significant differences between the regions of the tendons and therefore the entirety of the tendon can used through processing. When comparing the two different ten-dons (FIG. 9D) total protein is not different (P=0.93), but (FIG. 9H) TGF-β is statistically higher in Achilles than Patellar tendon (P=0.0045).

|  | F Value | P Value | Significant |
|---|---|---|---|
| 9A | F (2, 15) = 0.01075 | 0.9893 | No |
| 9B | F (2, 15) = 1.069 | 0.3680 | No |
| 9C | F (2, 33) = 0.9342 | 0.4030 | No |
| 9E | F (2, 15) = 1.849 | 0.1915 | No |
| 9F | F (2, 15) = 0.3373 | 0.7190 | No |
| 9G | F (2, 33) = 0.7912 | 0.4617 | No |

As shown in FIG. 10, filtering effectively eliminated collagenase activity. Decellularized tendon was treated with collagenase to improve form-factor of DTM. 100 kDa filters were highly effective in eliminating the collagenase activity in the final product. ANOVA indicates that the groups have significant differences (F (4, 22)=18.06, p<0.0001). Impor-tantly, there are no significant differences in collagenase activity between native and 100 kDa filtered samples.

| Comparison | p Value | Significant |
|---|---|---|
| Native vs. Decellularized | 0.9919 | No |
| Native vs. Collagenase No Filter | <0.0001 | **** |
| Native vs. Collagenase 70 um Filter | 0.0116 | * |
| Native vs. Collagenase 100 kDa Filter | 0.9635 | No |
| Decellularized vs. Collagenase No Filter | <0.0001 | **** |
| Decellularized vs. Collagenase 70 um Filter | 0.0381 | * |
| Decellularized vs. Collagenase 100 kDa Filter | >0.9999 | No |
| Collagenase No Filter vs. Collagenase 70 um Filter | 0.0021 | ** |
| Collagenase No Filter vs. Collagenase 100 kDa Filter | <0.0001 | **** |
| Collagenase 70 um Filter vs. Collagenase 100 kDa Filter | 0.003 | ** |

As shown in FIG. 11, more bioactivity is retained in DTM than standard methods for decellularizing tendon with pep-sin. Tendons were digested following decellularization, using a solution containing Collagenase Type 1 (92.5 g tendon/g Collagenase 1) and 3 (185 g tendon/1 g Col 3), or using Pepsin given previous published methodologies (Farnebo et. al 2014, PMID: 24341855). ANOVA indicated significant differences between groups, F (3,11)=5.056, p=0.0193. Tukey's HSD post hoc shows pepsin has signifi-cantly less TGF-b (P=0.0249).

As shown in FIG. 15, the normalized TGFb content across four samples from four different donors, over the two processing steps. For each respective donor, the first column represents the amount of TGFb in the native tendon, the second column represents the amount of TGFb in the decellularized tendon, and the third column represents the amount of TGFb in the digested tendon. The percent changes across the processing steps is also described in the following table (percent increase is measured from native tendon to post collagenase processing):

| Donor | % Increase in TGF-b |
|---|---|
| #1 | 590.16 |
| #2 | 677.04 |
| #3 | 144.75 |
| #4 | 210.36 |

Differences in proliferation of cells plated on different surfaces was investigated (see, e.g., FIGS. 12A-C). Tissue culture plates were left untreated (control, "TC treated"), coated with collagen or with the DTM. Primary tenocytes (ZenBio #TEN-F) were plated at 20,000 cells/well and cell viability quantified using the Presto Blue (Thermo Fisher) at (A) 48 hours or (B) 7 days after plating, generating signifi-cantly different growth rates (C). (ANOVA=F (3,26)=10.6, p<0.0001).

| | Comparison | p Value | Significant |
|---|---|---|---|
| Day 2 | TC Treated vs. Collagen Coat | 0.8816 | No |
| | TC Treated vs. DTM | 0.0025 | ** |
| | Collagen Coat vs. DTM | 0.0089 | ** |
| Day 7 | TC Treated vs. Collagen Coat | 0.1792 | No |
| | TC Treated vs. DTM | <0.0001 | *** |
| | Collagen Coat vs. DTM | <0.0001 | *** |

The invention claimed is:

1. A decellularized tendon matrix (DTM) composition produced by a method comprising:

decellularizing a minced native tendon tissue with a DNAse solution for about 0.5 to 2 hours thereby producing a decellularized tendon;

contacting the decellularized tendon with an enzymatic solution comprising a matrix metalloproteinase (MMP) to produce a digested, decellularized tendon;

lyophilizing the digested, decellularized tendon to pro-duce a lyophilized tendon;

reconstituting the lyophilized tendon to produce a DTM composition;

wherein the DTM retains at least 50% of growth factors present in the native tendon;

wherein the DTM is substantially free of TGFβ producing cells; and, wherein the method excludes decellularizing with anionic detergents comprising SDS and/or EDTA.

2. The DTM composition of claim 1, wherein the DNase solution comprises about 10 to about 100 Units of DNase per milliliter of solvent, about 25 to about 75 Units of DNase per milliliter of solvent, about 40 to about 60 Units of DNase per milliliter of solvent, about 40 to about 60 Units of DNase per milliliter of solvent, or about 50 Units of DNase per milli-liter of solvent.

3. The DTM composition of claim 1, wherein the decel-lularizing comprises contacting the tendon with a concen-tration of between about 4 milliliters and about 50 milliliters of the DNase solution per 1 gram of tendon, between about 5 milliliters and about 10 milliliters of the DNase solution per 1 gram of tendon, or between about 10 milliliters and about 50 milliliters of the DNase solution per 1 gram of tendon.

4. The DTM composition of claim 3, wherein the con-tacting optionally occurs on a shaker.

5. The DTM composition of claim 1, wherein the decel-lularizing further comprises:

washing the native tendon with phosphate buffered saline, and filtering the tendon.

6. The DTM composition of claim 5, wherein the native tendon is filtered through a 70 micrometer strainer using centrifugation at between about 1500 G to about 2500 G for between about 1 minute and about 15 minutes.

7. The DTM composition of claim 1, wherein the lyophilizing comprises freezing the digested, decellularized tendon at minus 80° C. for at least about 30 minutes.

8. The DTM composition of claim 1, wherein the MMP comprises collagenase.

9. The DTM composition of claim 8, wherein the collagenase is selected from the group consisting of Collagenase Type I, Collagenase Type III, and a combination thereof.

10. The DTM composition of claim 1, wherein the decellularized tendon is contacted with between about 10 milliliters and about 50 milliliters of the enzymatic solution per 1 gram of tendon, or with between about 5 milliliters and about 10 milliliters of the enzymatic solution per 1 gram of tendon.

11. The DTM composition of claim 1, wherein the decellularized tendon is contacted with the enzymatic solution for a period of about 24 hours, or about 12 hours.

12. The DTM composition of claim 1, wherein the decellularized tendon is contacted with the enzymatic solution at about 37° C.

13. The DTM composition of claim 1, wherein the reconstituting comprises mixing between about 2 microliters and about 5 microliters of solvent with about 1 milligram of lyophilized tendon.

14. The DTM composition of claim 1, wherein the DTM comprises less than 5% by weight of cellular material in the native tendon, less than 2% by weight of cellular material in the native tendon, less than 1% by weight of cellular material in the native tendon, or less than 0.1% by weight of cellular material in the native tendon.

15. The DTM composition of claim 1, wherein the DTM comprises greater than 90% by weight of TGF-β in the native tendon, greater than 95% by weight of TGF-β in the native tendon, or greater than 99% by weight of TGF-β in the native tendon, and wherein the DTM is substantially free of TGF-β producing cells.

16. The DTM composition of claim 1, wherein the DTM comprises less than 5% by weight of DNA in the native tendon, less than 2% by weight of DNA in the native tendon, less than 1% by weight of DNA in the native tendon, or less than 0.1% by weight of DNA in the native tendon, and wherein the DTM is substantially free of DNA.

17. The DTM composition of claim 1, wherein the minced native tendon tissue has a size of about 1 to 4 mm$^3$.

18. The DTM composition of claim 1, wherein the decellularizing process with the DNAse solution excluding anionic detergents is faster as compared to a decellularizing process that includes anionic detergents.

19. The DTM composition of claim 1, wherein the DNase solution is applied on the minced native tendon tissue for about 1 hour.

20. A tissue regeneration scaffold comprising a decellularized tendon matrix (DTM) material produced by a method comprising:

decellularizing the native tendon thereby producing a decellularized tendon;

contacting the decellularized tendon with an enzymatic solution comprising a matrix metalloproteinase (MMP) to produce a digested, decellularized tendon;

lyophilizing the digested, decellularized tendon to produce a lyophilized tendon; and reconstituting the lyophilized tendon to produce the tissue regeneration scaffold, wherein the DTM retains at least 50% of growth factors present in the native tendon, and wherein the method excludes decellularizing with anionic detergents comprising SDS and/or EDTA.

21. The tissue regeneration scaffold of claim 20, further comprising an excipient.

22. A decellularized tendon matrix (DTM) composition produced by a method comprising:

decellularizing a native tendon thereby producing a decellularized tendon;

contacting the decellularized tendon with about 10 milliliters to about 50 milliliters of an enzymatic solution per 1 gram of tendon, or about 5 milliliters to about 10 milliliters of the enzymatic solution per 1 gram of tendon, wherein the enzymatic solution comprises a matrix metalloproteinase (MMP) to produce a digested, decellularized tendon; and lyophilizing the digested, decellularized tendon to produce a lyophilized tendon, wherein the method excludes decellularizing with anionic detergents comprising SDS and/or EDTA.

* * * * *